US010670561B2

(12) United States Patent
Ewing et al.

(10) Patent No.: US 10,670,561 B2
(45) Date of Patent: Jun. 2, 2020

(54) DEVICE AND SYSTEM FOR SELECTIVE IONIZATION AND ANALYTE DETECTION AND METHOD OF USING THE SAME

(71) Applicant: Battelle Memorial Institute, Richland, WA (US)

(72) Inventors: Robert Ewing, Kennewick, WA (US); Blandina Valenzuela, Richland, WA (US); Eric Freeburg, Minneapolis, MN (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/258,338

(22) Filed: Jan. 25, 2019

(65) Prior Publication Data
US 2020/0025715 A1    Jan. 23, 2020

Related U.S. Application Data

(60) Provisional application No. 62/701,174, filed on Jul. 20, 2018.

(51) Int. Cl.
*H01J 49/14* (2006.01)
*H01J 49/26* (2006.01)
(Continued)

(52) U.S. Cl.
CPC ....... *G01N 27/622* (2013.01); *G01N 33/0057* (2013.01); *H01J 49/0077* (2013.01); *H01J 49/14* (2013.01); *H01J 49/26* (2013.01)

(58) Field of Classification Search
CPC .............. G01N 27/622; G01N 33/0057; H01J 49/0077; H01J 49/14; H01J 49/26
(Continued)

(56) References Cited

U.S. PATENT DOCUMENTS

| 5,234,838 A | 8/1993 | Bacon, Jr. |
| 6,777,670 B1 * | 8/2004 | Farnsworth ........... H01J 49/009 250/281 |

(Continued)

FOREIGN PATENT DOCUMENTS

| CN | 101752176 | 6/2010 |
| EP | 3 082 151 | 10/2016 |
| WO | WO 00/52432 | 9/2000 |

OTHER PUBLICATIONS

Ewing et al., "Proton-bound cluster ions in ion mobility spectrometry," *International Journal of Mass Spectrometry*, vol. 193, pp. 57-68, Jan. 29, 1999.

(Continued)

*Primary Examiner* — Nicole M Ippolito
(74) *Attorney, Agent, or Firm* — Klarquist Sparkman, LLP

(57) ABSTRACT

Disclosed herein are embodiments of a system for selectively ionizing samples that may comprise a plurality of different analytes that are not normally detectable using the same ionization technique. The disclosed system comprises a unique split flow tube that can be coupled with a plurality of ionization sources to facilitate using different ionization techniques for the same sample. Also disclosed herein are embodiments of a method for determining the presence of analytes in a sample, wherein the number and type of detectable analytes that can be identified is increased and sensitivity and selectivity are not sacrificed.

23 Claims, 13 Drawing Sheets

(51) Int. Cl.
  *G01N 27/62* (2006.01)
  *G01N 33/00* (2006.01)
  *H01J 49/00* (2006.01)

(58) Field of Classification Search
  USPC .............................. 250/281, 282, 283, 288
  See application file for complete search history.

(56) References Cited

U.S. PATENT DOCUMENTS

| | | |
|---|---|---|
| 9,123,520 B2 | 9/2015 | Ewing et al. |
| 10,119,937 B2 | 11/2018 | Ewing et al. |
| 2006/0249671 A1* | 11/2006 | Karpetsky ............ G01N 27/624 250/288 |
| 2006/0289746 A1* | 12/2006 | Raznikov ............. G01N 27/622 250/294 |
| 2008/0149824 A1 | 6/2008 | Miller |
| 2012/0126109 A1 | 5/2012 | Wu |
| 2013/0161509 A1* | 6/2013 | Munchmeyer ....... G01N 27/622 250/282 |
| 2013/0260478 A1 | 10/2013 | Ewing et al. |
| 2018/0017529 A1 | 1/2018 | Ewing et al. |
| 2018/0068841 A1* | 3/2018 | Wilton .................. H01J 49/147 |
| 2018/0323050 A1* | 11/2018 | Smith ................. H01J 49/0031 |
| 2019/0285584 A1* | 9/2019 | Wu ....................... H01J 49/004 |

OTHER PUBLICATIONS

International Search Report and Written Opinion issued for International Application No. PCT/US2017/028758, dated Aug. 1, 2017.
Keller et al., "Detection of designer drugs in human hair by ion mobility spectrometry (IMS)," *Forensic Science International*, vol. 94, pp. 55-63, Jan. 31, 1997.
Puton et al., "Ion mobility spectrometers with doped gases," *Talanta*, vol. 76, pp. 978-987, May 29, 2008.
Satoh et al., "Ion mobility spectrometric analysis of vaporous chemical warfare agents by the instrument with corona discharge ionization ammonia dopant ambient temperature operation," *Analytica Chimica Acta*, vol. 865, pp. 39-52, Feb. 4, 2015.
Verkouteren et al., Reliability of ion mobility spectrometry for qualitative analysis of complex, multicomponent illicit drug samples, *Forensic Science International*, vol. 206, pp. 190-196, Sep. 15, 2010.
Waraska et al., "Dopants and gas modifiers in ion mobility spectrometry," *Trends in Analytical Chemistry*, vol. 82, pp. 237-249, Jun. 11, 2016.
International Search Report and Written Opinion issued for International Application No. PCT/US2019/042460 dated Oct. 7, 2019.

* cited by examiner

DEVICE AND SYSTEM FOR SELECTIVE IONIZATION AND ANALYTE DETECTION AND METHOD OF USING THE SAME

CROSS REFERENCE TO RELATED APPLICATION

This application claims the benefit of the earlier filing date of U.S. Provisional Application No. 62/701,174, filed on Jul. 20, 2018; this prior application is incorporated herein by reference in its entirety.

ACKNOWLEDGMENT OF GOVERNMENT SUPPORT

This invention was made with Government support under Contract No. DE-AC05-76RL01830 awarded by the U.S. Department of Energy. The Government has certain rights in the invention.

FIELD

Disclosed herein are embodiments of a system and method for selectively ionizing and analyzing analytes using a unique split flow tube and multiple ionization sources.

BACKGROUND

Low-level detection of threat agents and illicit substances (e.g., explosive, narcotics and organophosphorus compounds (OPCs)) remains a long-standing goal of modern instrument platforms. Analytical techniques for direct vapor detection of threat agents and illicit substances remain limited because significant improvements in sensitivity must yet be attained if automated technologies are to be of practical use. For example, equilibrium vapor pressure (saturated) of RDX explosive at 25° C. provide a concentration of ~5 parts-per-trillion (ppt). Because real-world analyses must achieve detection below saturation levels, sensitivity must be substantially better than this 5 ppt threshold. To complicate matters, improvements in sensitivity without improvements in selectivity are counterproductive, as increasing sensitivity effectively raises the chemical noise, which offsets improvements to upstream components. Also, the ability to detect multiple analytes from a single sampling event is limited by the fact that detection methods used for certain analytes do not always work to detect other types of analytes. As such, multiple sampling events and/or instruments must be utilized to detect various threat agents and/or illicit substances. Accordingly, new methods and systems are needed to provide accurate detection of such analytes, particularly at ultra-low levels, and without requiring multiple sampling events and/or analyses.

SUMMARY

Disclosed herein are embodiments of a split flow tube that can be used to facilitate selective ionization of analytes using a plurality of ionization sources. In some embodiments, the split flow tube comprises a distal end configured to be coupled to a detection apparatus; a proximal end; a barrier positioned within the split flow tube so as to separate an internal volume of the split flow tube into two or more reaction regions and extending along a length of the split flow tube; a first opening configured to accept a first ionization source, and a second opening in the split flow tube configured to accept a sample introduction inlet; and an exit opening formed at the distal end of the split flow tube. In some embodiments, the split flow tube can further comprise an opening configured to introduce a carrier gas into a reaction region and/or a third opening configured to accept a second ionization source. Representative configurations of the split flow tube are described herein.

Also disclosed herein are embodiments of a system comprising a split flow tube embodiment according to the present disclosure, a sample introduction region coupled to a sample introduction inlet of the split flow tube; and a detection apparatus coupled to the distal end of the split flow tube. In some embodiments, the detection apparatus is a mass spectrometer, an ion mobility spectrometer, or a differential ion mobility spectrometer. The system can be configured to comprise a first ionization source and the second ionization source, which can be the same or different. Representative ionization sources that can be used are described herein. In some embodiments, the system can further comprise a first ionization source coupled to an opening of the split flow tube and a second ionization source coupled to an opening of the split flow tube. The system also can comprise one or more pumps connected to the split flow tube and/or the detection apparatus. Also disclosed herein are embodiments of using the disclosed split flow tube and/or system embodiments.

The foregoing and other objects and features of the present disclosure will become more apparent from the following detailed description, which proceeds with reference to the accompanying figures.

BRIEF DESCRIPTION OF THE DRAWINGS

FIGS. 9A and 9B are mass spectra obtained from analyzing triaminotrinitrobenzene using a reverse flow corona discharge ionization source and a split flow tube as described herein, wherein FIG. 9A is a background spectrum and FIG. 9B shows the TATB analyte ion peak (peak "A") observed as the proton abstracted ion ([M−H]⁻) at m/z=257.

DETAILED DESCRIPTION

I. Overview of Terms and Abbreviations

Figure 1:
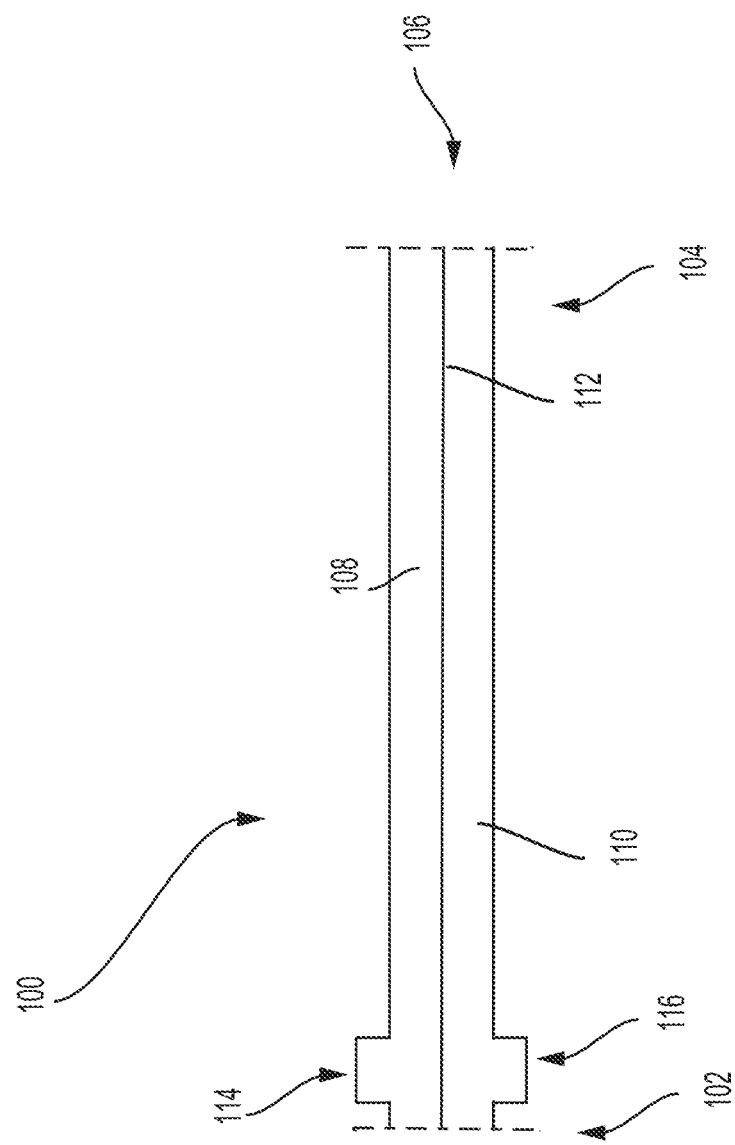
FIG. 1 shows a cross-sectional view of a split flow tube embodiment comprising a barrier that separates the internal volume of the split flow tube into two separate reaction regions.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

While preferred embodiments of the present invention will be described, from the description, it will be apparent that various modifications, alterations, and substitutions may be made without departing from the scope of the invention as set forth in the claims listed hereafter. Further, while the present disclosure includes references to detection of chemical explosives, illicit drugs, and organophosphorous compounds, some embodiments of the present disclosure are intended to cover various and multiple threat agents, as well as chemicals used to identify the presence of threat agents including explosive taggants and the like.

To facilitate review of the various embodiments of the disclosure, the following explanations of specific terms are provided.

Adduct Ions: Ions formed in a reaction region of a split flow tube by collisions between reactant ions and sample vapor, or dopants (or ions thereof) and sample vapor. Chemical adduct ions and dopant adduct ions are examples of adduct ions. In particular disclosed embodiments, adduct ions include at least one analyte of interest as a component of the adduct ion.

Analyte Ions: Ions formed in a reaction region of a split flow tube that comprise ionized analyte species.

Chemical Adduct Ions: Ions formed between reactant ions and an analyte (or ions thereof) present in sample vapor.

Dopant Adduct Ions: Ions formed between dopants (or ions thereof) and analytes (or ions thereof) present in sample vapor. In some embodiments, a dopant adduct ion can further include a reactant ion.

Detection Apparatus: An apparatus capable of detecting the presence of adduct ions and/or analyte ions formed in a reaction region of a split flow tube. In some embodiments, a suitable detection apparatus includes an ion detector, such as a mass spectrometer, an ion mobility spectrometer, a differential ion mobility spectrometer, or the like.

Explosives (or Explosive Compounds): A class of compounds encompassing any chemical substance or compound that when detonated (e.g., by heating or striking, or other detonation events) undergoes a rapid chemical change, producing a large and sudden release of energy (e.g., energy in the form of a gas), such as an explosion; and/or chemical compounds (e.g., oxidizing salts, such as potassium chlorate) that are not inherently explosive, but that become explosive when mixed with another component that promotes the explosion.

Low Concentration: As used herein, this term means an analyte concentration at or below 100 parts-per-trillion (ppt) prior to being combined with a carrier gas at selected carrier gas pressures above 100 Torr (0.13 atm).

Reactant Ions: Ions that are formed by ionization of a carrier gas (with or without a dopant). Reactant ions can react with analyte species present in sample vapors upon collision in a reaction region of a split flow tube embodiment, forming adduct ions of interest and/or analyte ions of interest. In particular embodiments, certain reactant ions have a selectivity for binding to at least one analyte greater than the selectivity for binding to another analyte or constituent present in a reaction region of a split flow tube.

Sample Introduction Region: A region that is configured to house or otherwise contain a sample such that the sample can be vaporized and introduced into a split flow tube for analysis. In some embodiments, a sample introduction region can comprise or can be coupled to a sample introduction inlet through which sample vapors can enter a split flow tube.

Opening (of a split flow tube): An inlet, hole, or other such conduit that facilitates delivery of ions, analytes, sample vapors, dopants, or other such species into the interior of a split flow tube.

Reaction Region: A region within a split flow tube defined by a barrier and an inner wall of the split flow tube.

Sampling Event: A sampling event occurs when sample vapors are produced from a sample and introduced into a split flow tube by way of a sample introduction inlet. In method embodiments of the present disclosure using a "single sampling event," sample vapors only need to be introduced once into a split flow tube for analysis using two (or more) different ionization techniques to evaluate the presence of any analytes in a sample. This is in contrast to a technique that requires two or more sampling events to facilitate using two (or more) different ionization techniques to evaluate the presence of any analytes in a sample.

II. Introduction

Current state of the art trace detection methods for explosives, chemical threat agents, other threat agent signatures, and illicit drugs have remained long-standing goals of modern instrument platforms; however, analytical techniques for direct vapor detection of such compounds remain limited because significant improvements in sensitivity must yet be attained if automated technologies are to be of practical use. For example, equilibrium vapor pressure (saturated) of RDX explosive at 25° C. provide a concentration of ~5 parts-per-trillion (ppt) or 5 in $10^{12}$. Because real-world analyses must achieve detection below saturation levels, sensitivity must be substantially better than this 5 ppt threshold. To complicate matters, improvements in sensitivity without improvements in selectivity are counterproductive, as increasing sensitivity effectively raises the chemical noise, which offsets improvements to upstream components. Thus detecting threat agent and/or illicit drug vapors requires significant increases in sensitivity along with subsequent increases in selectivity. While some sensitivity and selectivity improvements have been achieved with mass spectrometry (MS)-based analytical approaches including, e.g., Selected Ion Flow Tube (SIFT) Mass Spectrometry (MS) or (SIFT-MS); Proton Transfer Reaction Mass Spectrometry (PTR-MS); and Atmospheric Pressure Chemical Ionization Mass Spectrometry (APCI-MS), none of these approaches selectively determines vapors from explosives and other threat agents below ppt levels in real-time.

Additionally, conventional devices and methods for detecting analytes like threat agents and/or illicit drugs are limited in the sense that the ionization mechanism used to produce the ions and/or adducts needed for detection must be varied depending on the analyte of interest. This need for separate detection sequences prevents the ability to analyze a sample for all possible analytes with a single sampling event. For example, while certain ionization techniques can be used to provide reactant ions (e.g., nitrate ions) that are capable of interacting with certain explosives (e.g., nitroamines and/or nitrate esters), these reactant ions are not capable of ionizing certain nitroaromatic compounds, such as TNT. As such, separate (or multiple) sampling events with different ionization techniques must be used to determine the presence of all such analytes in a sample. Additionally, while certain ionization techniques produce reactant ion species that can be used to ionize certain explosives, the same reactant ions generally cannot be used to ionize other species of interest, such as illicit drugs and/or OPCs. As such, different instrumentation, several sampling events, and/or detection steps must be used to analyze a single sample for the presence of a combination of analytes.

The present disclosure describes embodiments of a split flow tube component and system embodiments comprising the same. Also disclosed are method embodiments that can be used to analyze a single sample or a combination of samples that may comprise a plurality of different analytes concurrently in a single sampling event without the need to carry out multiple sampling events and/or detection steps and without having to switch ionization sources or operational modes during analysis. The disclosed system embodiments provide a mechanism for using different ionization sources concurrently, or substantially concurrently, by providing a split flow tube capable of isolating reactant ion species, dopant species, and/or analyte species into separate "reaction regions" thereby providing the ability to use plural ionization sources in the same method and during a single sampling event. The disclosed system and method embodiments thus allow a user to analyze a plurality of different analyte species that may be present in a sample (or combination of samples) with the same system without having to conduct multiple sampling events and without having to physically modify the device set-up. Furthermore, the disclosed system and method embodiments greatly improve selectivity and enhances the number of detectable species with a single system.

III. Split Flow Tube and System Embodiments

Disclosed herein are embodiments of a split flow tube and a corresponding system comprising the split flow tube for analyzing a sample (or a combination of samples) to determine whether the sample includes one or more analytes of interest. In some embodiments, the split flow tube is a hollow tube having an internal volume and that comprises one or more barriers positioned within the split flow tube so as to define separated reaction regions within the internal volume of the split flow tube. Sample vapors can be split and diverted through the separated reaction regions so that sample vapors in one reaction region are separated from sample vapors in a different reaction region. The split flow tube can be designed for use with one or more ionization sources, one or more sample introduction regions, and one or more detectors.

An illustration of a simplified split flow tube is provided by FIG. 1. As illustrated in FIG. 1, split flow tube 100 comprises a proximal end 102 configured to be coupled with a sample introduction region (not illustrated) and a distal end 104 configured to be coupled to a detection apparatus (not illustrated). The split flow tube further comprises an exit opening 106 at distal end 104 of split flow tube 100. The split flow tube further comprises two reaction regions 108 and 110 that are separated by an internal barrier 112 that extends a length of the split flow tube. In some embodiments, such as with split flow tube 100 in FIG. 1, openings 114 and 116 can be provided that facilitate coupling the split flow tube to separate ionization sources (not illustrated). Such connection regions need not be used in all embodiments. The split flow tube can further comprise additional connection regions that are connected to a sample inlet through which sample vapors and/or carrier gas can be introduced to the split flow tube. The split flow tube typically is made of a metal material, but any suitable material could be used as long as it is compatible with ionized species, carrier gases, and/or other components that flow through the tube. The barrier can be made of any suitable material that resists cross flow of ionized species, flow gases, and the like between the different reaction regions. In particular disclosed embodiments, the barrier is made of a metal material and typically is made to have a particular thickness, such as 0.02 mm to 10 mm, or 0.1 mm to 2 mm. The split flow tube can be designed to comprise a plurality of barriers thereby defining a plurality of reaction regions, with particular embodiments having one, two, three, or four barriers defining two to five reaction regions, particularly two, three, four, or five different reaction regions. In particular disclosed embodiments, the split flow tube comprises one barrier and two separated reaction regions.

In some embodiments, the split flow tube can be an atmospheric flow tube comprising one or more barriers as described above. In yet additional embodiments, the split flow tube can comprise a plurality of reaction regions, which, independently, can comprise a plurality of metal rings with central ring openings that are separated by a dielectric material (e.g., polytetrafluoroethylene (PTFE), ceramics, quartz, glass, boron nitride, or another insulating material). Voltages applied to the metal rings establish an electrical field that moves ions in one or more of the reaction regions from the ionization source to the detector. Electrical field strength may be varied. In some embodiments, field strength may be varied in the reaction region from about 2000 V (100 V/cm) to about 100 V (5 V/cm), but field strength is not intended to be limited thereto. A voltage gradient can be adjusted to increase the ion residence time or decrease the ion residence time in each independent reaction region. Voltages are selected such that residence times for reactant ions in the reaction region are sufficient to form chemical adduct ions between reactant ions and analytes and/or that are sufficient for a reactant ion to ionize an analyte species to provide analyte ions.

Each reaction region of the split flow tube individually can include a length that, during operation, provides a sufficient number of collisions between reactant ions and any analytes of interest present within the reaction regions (as provided by the sample vapor). Typically, the split flow tube has a length dimension that is greater than the cross-section (e.g., diameter) dimension. In some embodiments, each reaction region has the same length and the length ranges from 1 cm to 500 cm, such as 10 cm to 200 cm, or 25 cm to 100 cm. In some embodiments, the split flow tube can have an outer diameter and an inner diameter. In some embodiments, the inner diameter can range from 0.3 cm to 12 cm, such as 0.6 cm to 8 cm, or 1.2 cm to 5 cm.

The multiple reaction regions of the split flow tube can independently be coupled to its own ionization source, which can be the same or different as the ionization source coupled to other reaction regions. In particular embodiments, the ionization sources are different for each reaction region. The ionization source can be physically coupled to openings of the split flow tube using appropriate connections (e.g., connection regions, electronic connections, and the like). In some embodiments, the ionization source is selected for use with mass spectrometric detection and/or ion mobility spectrometric detection. The ionization source typically is one that is capable of ionizing a carrier gas with or without a dopant so as to produce reactant ions which can be used with the disclosed system. Some ionization sources suitable for use with the disclosed system include, but are not limited to, static electric discharge sources; varying electric discharge sources; plasma torch sources; photoemission ionization sources; electrospray ionization sources; photoionization sources, and combinations thereof. In yet additional embodiments, the ionization source may be a radioactive decay ionization source. In yet additional embodiments, the ionization source may be a non-radioactive ionization source. Some exemplary ionization sources include, but are not limited to $^{63}$Ni sources, corona sources; corona discharge sources; distributed plasma ionization sources (DPIS); open DPIS sources; enclosed DPIS sources; electrospray ionization (ESI) sources; atmospheric pressure ionization (API) sources; atmospheric pressure (AP) chemical ionization (APCI) sources; AP glow discharge ionization (GD) (APGD) sources; AP photo ionization sources; dielectric ionization sources (DIS); dielectric barrier discharge ionization (DBD) sources; dielectric plasma ionization (DPI) sources; dielectric isolated plasma ionization sources; photoemission ionization sources; components of these various sources; and combinations of these sources and components. In particular disclosed embodiments, the ionization sources used with the split flow tube can include pulsed ionization sources; time-varying discharge sources (e.g., dielectric barrier discharge sources); corona ionization sources; LED ionization sources; and combinations of these various ionization sources.

Figure 2:
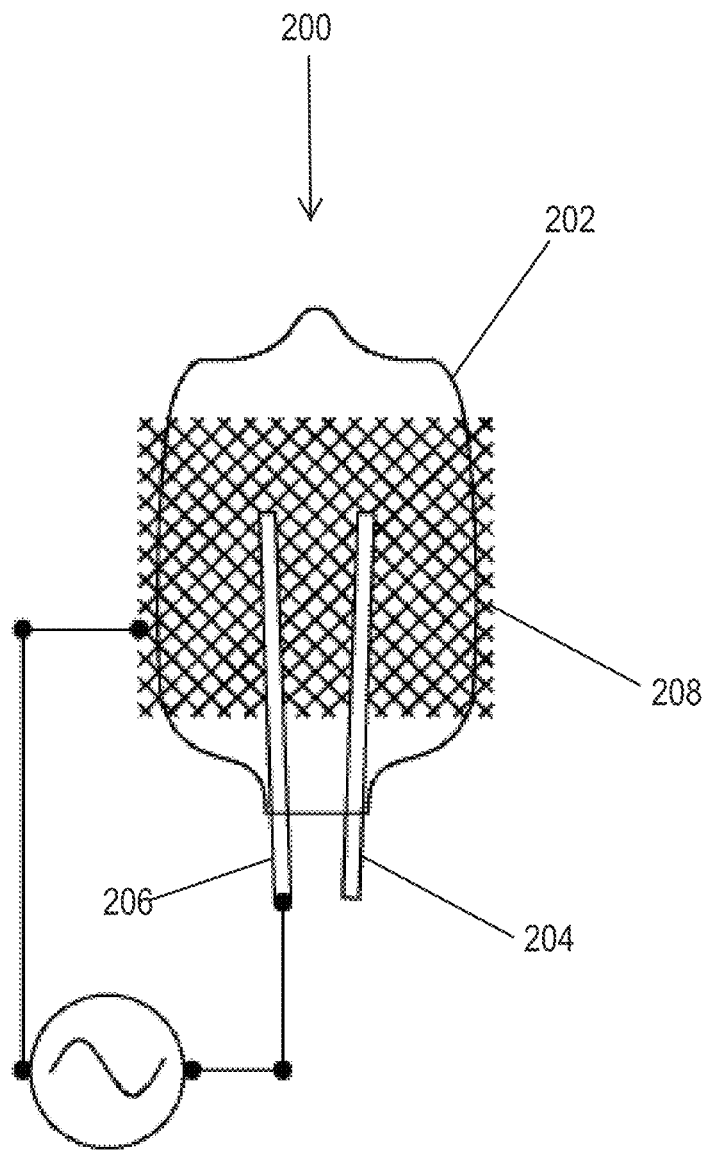
FIG. 2 shows a representative ionization source for producing reactant ions that can be introduced into a split flow tube embodiment as described herein.

FIG. 2 shows an exemplary ionization source of a DBD-type that can be used in certain embodiments of the system disclosed herein. This particular ionization source 200 of FIG. 2 includes a glass bulb 202 filled with neon gas, or another excitation gas. Gas selection is not limited. The bulb includes at least two electrodes 204 and 206 that provide excitation of the neon (or other enclosed) gas in the bulb. Supporting electronics provide power to the bulb to generate the ion (e.g., conductive) plasma. In some embodiments, the bulb may be illuminated with a DC current. In some embodiments, the bulb may be illuminated with an AC current.

In some embodiments, the glass bulb includes an external surface containing a dielectric material in which the bulb serves as a primary conductor dielectric medium. In ionization source 200, the bulb includes a metal mesh (e.g., stainless steel mesh) 208 placed in close proximity to, or in contact with a dielectric material (not shown) on the exterior surface of the bulb. The wire mesh provides a large surface area from which plasma discharges can originate.

In some embodiments, one electrode serves as a primary electrode and the wire mesh serves as a secondary electrode. In the embodiment shown in FIG. 2, a conductive plasma may be generated with a single bulb electrode connected as shown.

In some embodiments, when a high (kHz) frequency alternating current (AC) is placed across the single electrode that is connected to the bulb, and the conducting mesh (e.g., stainless steel) electrode located external to the bulb, a plasma discharge may be generated at the edges of the external conducting electrode. Discharge of the plasma occurs when the voltage potential between the conducting electrode and the plasma within the bulb reaches the breakdown voltage of the gas at a given temperature, pressure, and humidity.

Figure 3:
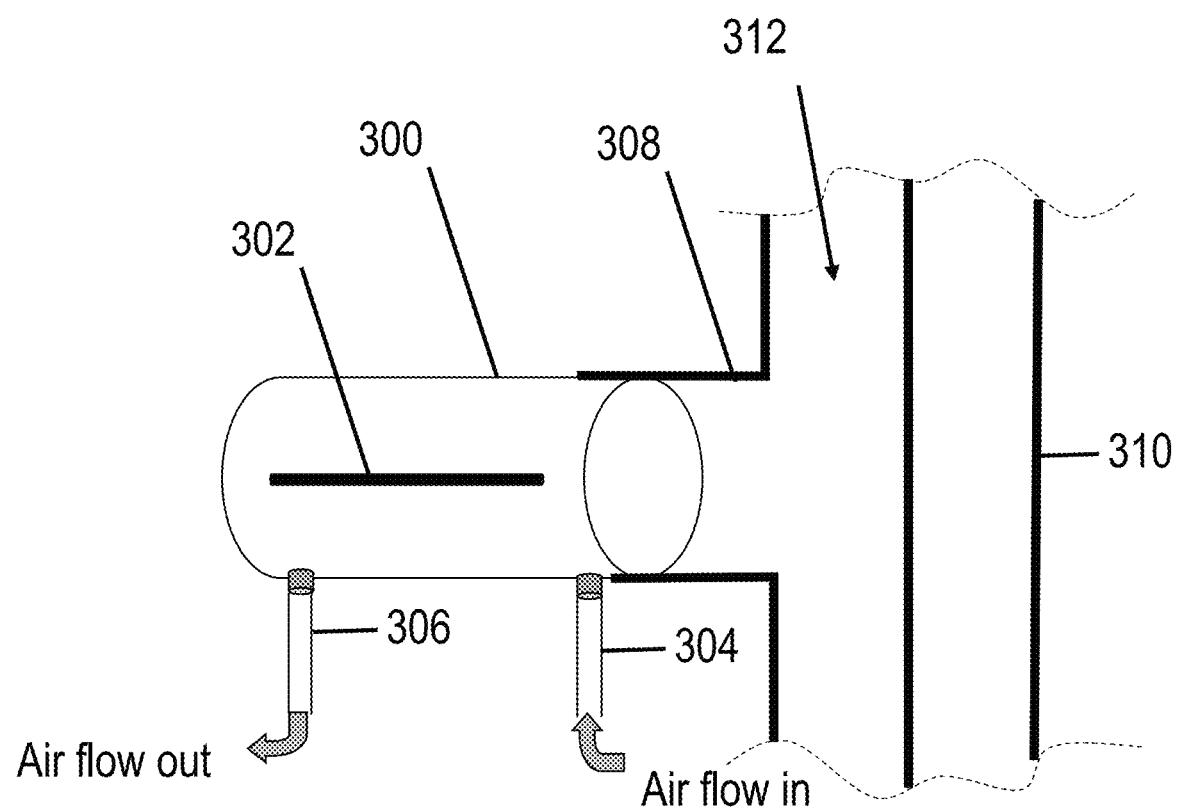
FIG. 3 is a schematic illustration of another representative ionization source that can be used with reverse air flow to change the ion chemistry of reactant ions entering a split flow tube embodiment.

Another exemplary type of ionization source that can be used in the disclosed system and method is a corona discharge ionization source. In particular disclosed embodiments, the corona discharge ionization source is used in combination with reverse air flow so as to provide the ability to flush certain neutral vapors, created by the discharge, out of the ionization region thereby changing the chemical make-up of the reactant ions present in the split flow tube (also referred to herein as reverse corona discharge ionization). A representative schematic of a reverse flow corona discharge apparatus is illustrated in FIG. 3. With reference to FIG. 3, reverse flow corona discharge apparatus 300 comprises a corona discharge needle 302, an air inlet tube 304, and an air outlet tube 306. The reverse flow corona discharge apparatus is coupled to an opening 308 of a split flow tube embodiment 310 such that ion flow from the corona discharge needle 302 enters a reaction region 312 of the split flow tube 310. Air flow can be introduced into reverse flow corona discharge apparatus 300 via air inlet tube 304 so that air flows through the reverse flow corona discharge apparatus in a reverse direction (relative to ion flow) and thus can direct unwanted neutral vapors out of the ionization source through air outlet tube 306.

In various embodiments, the selected ionization source can be operated in a pulsed, continuous, or variable manner depending on the applied waveform or the combination of electric waveforms applied. The circuit that drives the ionization source remains functional because the dielectric material prevents a true electric short from occurring while still enabling the discharge.

In some embodiments, discharge by the ionization source in the reaction region initially produces free electrons; however, when a sufficient carrier gas density is present, electrons are transferred to the gas medium which forms reactant ions, described further herein. Reactant ions then react with analytes present in sample vapors upon collision in the reaction region, forming adduct ions of interest or by ionizing analytes present in the sample vapor by charge transfer.

In some embodiments, the ionization sources independently can be coupled to a reaction region downstream from where a sample is introduced, but position is not intended to be limited in all embodiments. In some embodiments, the sample introduction region and/or a sample introduction inlet can be located at the proximal end of the split flow tube and before openings of the split flow tube used for coupling to an ionization source, relative to the proximal end. In some other embodiments, the sample introduction region and/or a sample introduction inlet can be located at the proximal end of the split flow tube and after openings of the split flow tube used for coupling to an ionization source, relative to the proximal end. In particular disclosed embodiments, an ionization source can be coupled adjacent a carrier gas inlet to ionize the carrier gas delivered through the carrier gas inlet into a reaction region to form the reactant ions.

The system can further comprise a detector. The detector can be any mass-selective or mobility-selective detector capable of detecting the presence of ions. In particular disclosed embodiments, the detector can be a mass-selective detector, such as a mass spectrometer. In other embodiments, the detector may be an Ion Mobility Spectrometer (IMS) or a Differential Mobility Spectrometer (DMS). The detector may be coupled at, or in proximity to, an exit opening of the split flow tube to detect any analyte ions and/or adduct ions flowing through the multiple reaction regions. In some embodiments, the detector can be coupled to the split flow tube such that the multiple reaction regions are coupled to the detector in a manner that allows any species within the reaction regions to be delivered to the detector separately. In yet additional embodiments, the detector can be coupled to the split flow tube in a manner such that any species within the reaction regions can first be recombined, such as in a drift region, and then delivered to the detector as a mixture.

Figure 4:
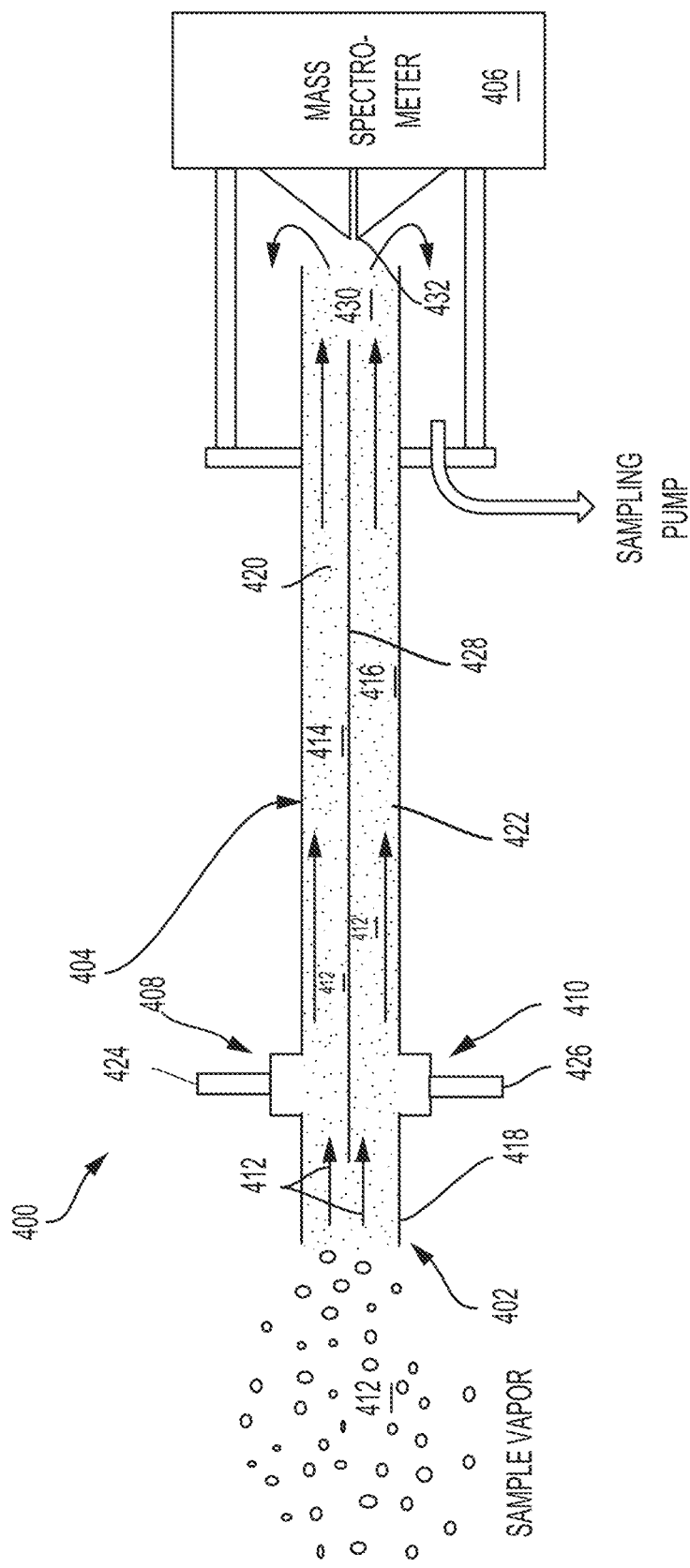
FIG. 4 is a schematic illustration of a representative system comprising a sample introduction region, a split flow tube embodiment, and a detection apparatus.

A representative system is illustrated in FIG. 4. With reference to FIG. 4, system 400 comprises a sample introduction region 402, which is coupled to a split flow tube 404. Split flow tube 404 is further coupled to a detection apparatus, such as mass spectrometer 406. While particular ionization sources are not illustrated, they can be coupled to split flow tube 404 using appropriate connections to openings 408 and 410. Also, suitable pumps and/or electrodes (not illustrated) can be coupled to the system to control ion flow through split flow tube 404. Additional aspects concerning system 400 are described herein.

IV. Methods

Disclosed herein are embodiments of a method for analyzing a sample to determine if it contains particular analytes, such as those discussed below. In some embodiments, the method comprises introducing a sample vapor and one or more reactant ions, dopants, or a combination thereof into a split flow tube embodiment according to the present disclosure. In some embodiments, the method can further comprise ionizing a carrier gas, forming a dopant from a dopant source, or a combination thereof so as to provide the one or more reactant ions, dopants, or the combination thereof using a first ionization source, a second ionization source, or a combination thereof. In some embodiments, the method can further comprise forming adduct ions or ionized analytes in one or more reaction regions of the split flow tube by allowing sufficient residence time in the one or more reaction regions such that reactant ions can interact with analytes that may be present in the sample, such as a residence time between 0.10 seconds and 30 seconds. The residence time can be controlled with a carrier gas flow, an electric field applied along the length of the reaction regions, or a combination of both the carrier gas flow and the electric field.

In some embodiments, an analyte contained within a vial or other container and capable of emitting a vapor is placed in a sample introduction region, which can be fluidly and/or physically coupled to a sample introduction inlet that directs the sample vapor to the split flow tube. In some embodiments, a sample vapor is present in an environment and is drawn directly into a sample introduction inlet by suction. In yet some additional embodiments, a sample vapor is drawn directly into the sample introduction inlet of the reaction region from the ambient environment by suction. In some embodiments, a solid surface containing a surface residue(s) may be placed in the sample introduction region. In some embodiments, a solid surface (e.g., wipes, swabs, substrates, or other solid objects) containing a solid sample may be placed in the sample introduction region. Exemplary surfaces include, but not limited to, sample slides, sample swipes, and/or other solid surfaces. In some embodiments, samples in the form of surface residues and/or surface solids on a solid surface can be desorbed from the solid surface to transfer the residues and/or surface solids into the gas phase, for example, by application of heat (such as by using thermal desorption).

In particular disclosed method embodiments of using the disclosed system, sample vapors comprising analytes may be introduced into each reaction region in a carrier gas that distributes within each reaction region equalizing the concentration of the vapor within each reaction region. Carrier gases include, but are not limited to, e.g., air, nitrogen ($N_2$), argon (Ar), helium (He), oxygen ($O_2$), carbon dioxide ($CO_2$), other inert gases, and combinations of these various gases. In a preferred embodiment, the carrier gas includes ambient air. In some embodiments, a carrier gas may be used to introduce sample vapors into the reaction region. Pressures of the carrier gas in the reaction region are preferably over 100 Torr.

FIG. 4 provides a schematic diagram of an exemplary system 400 comprising a split flow tube for detecting various analytes, including OPCs, illicit drugs, explosives, and the like. The system delivers peak intensities corresponding to vapor levels from detected analytes of interest. With reference to FIG. 4, sample vapors 412, which may contain analytes of interest, are introduced to two separated reaction regions 414 and 416 of the split flow tube 404 in various ways. In some embodiments, one or more vapors that may comprise analytes of interest may be introduced to the reaction region, for example, through a sample introduction inlet 418. In some embodiments, a sample gas including one or more sample vapors 412 that may comprise analytes of interest may be introduced to the reaction regions 414 and 416 for example via sample introduction inlet 418. In some embodiments, a dopant from a dopant vapor source can be mixed with the sample gas including one or more sample vapors 412 in one or more of reaction regions 414 or 416. In some embodiments, different dopants can be used by using different dopant vapor sources. The dopant can be mixed with sample vapors 412 before or after they enter any reaction region(s).

Sample vapors introduced for analysis may be pushed or pulled by suction. Once in the reaction regions, reactant ions 420 and 422, which are generated by ionization of a carrier gas with ionization sources 424 and 426, interact with vapors 412 and 412' introduced into the corresponding reaction region. In some embodiments using a dopant to detect analytes of interest, the ionized carrier gas can also interact with dopants when introduced into reaction regions 414 and 416. Positive ions are generated, for example, when a high energy electron emitted from one or more of the ionization sources collides with the carrier gas and removes an electron from the carrier gas producing a positive ion, for example $N_2^+$. In an exemplary process, multiple collisions occur within one or both of the reaction regions (depending on the ionization source selected and/or analytes of interest for detection) at or near atmospheric pressure resulting in a series of reactions that ultimately yield protonated species. However, pressures are not limited. Dopants, analytes, or other molecular species (e.g., contaminants) introduced in the different reaction regions may then be ionized by transfer of protons, which transfer is governed by relative proton affinities. Typically, molecular species with the highest proton affinity are observed. Along with generating positive ions, negative ions are also formed. A high energy electron is reduced to near thermal energies after multiple collisions. These near thermal electrons can then be captured by molecular species and form a variety of anions resulting from gas-phase reactions. Examples of such ions include, $O_2^-$, $CO_3^-$, $NO_2^-$, $Cl^-$, $NO_3^-$ and other species with a high electron affinity. Ionization of the analyte can occur with either positive or negative ions by mechanisms such as proton transfer, electron transfer, proton abstraction, or via adduct formation between an ionized species and another compound. For example, adduct ions described herein are formed by reactions between analytes of interest (e.g., certain explosives, OPCs, and/or illicit drugs) and added dopants (e.g., amines, such as secondary or tertiary amines; or OPCs), which forms dopant adduct ions; or from the ionization of the carrier gas (e.g., nitrate), which forms reactant ions that can form chemical adduct ions with analytes. In some embodiments, analytes are ionized by reactant ions so as to become charged species (or "analyte ions") that can then be detected. Solely by way of example, a nitroaromatic, like TNT, can interact with a reactant ion that facilitates loss of a proton from the TNT molecule, thus resulting in a charged TNT species that can be detected. In some embodiments, detecting adduct ions confirms the presence of the analytes of interest. In additional embodiments, detecting adduct ions (e.g., dopant adduct ions) formed between a dopant and any analytes of interest confirms the presence of the analytes of interest. In additional embodiments that do not utilize a dopant, detecting adduct ions (e.g., chemical adduct ions) formed between the carrier gas and any analytes of interest confirms the presence of the analytes of interest. In yet additional embodiments, detecting a charged analyte species (e.g., analyte ions) confirms the presence of the analytes of interest.

With further reference to FIG. 4, reactant ions (e.g., formed by ionization of air or carrier gas), analytes (e.g., analytes present in sample vapor 412 and/or 412'), and/or dopants when introduced into reaction regions 414 and 416 react forming adduct ions and/or analyte ions described herein that are subsequently detected in the detection apparatus, such as mass spectrometer 406. At a point in split flow tube 404, barrier 428 can terminate and adduct ions and/or analyte ions can be recombined into a single drift region 430 just prior to entering the detection apparatus. Excess carrier gas exits the reaction region immediately prior to the inlet 432 of the mass spectrometer 406, but exit location is not limited thereto, as will be understood by those of ordinary skill in the art of mass spectrometry, with the benefit of the present disclosure. In some embodiments, adduct ions are subsequently delivered to, and detected in, an ion detector, where the detection signal for adduct ions and/or analyte ions of interest may be monitored and determined. The detector determines the presence or absence of the adduct ions and/or analyte ions. Sensitivity or an increase in response can be improved by providing additional collisions between the reactant ions and analytes of interest. The number of collisions between the reactant ions typically is defined by the amount of time reactant ions and analyte molecules are present in the reaction region. Optimizing the detection signal for the adduct ions and/or analyte ions when present includes adjusting the number of collisions between the reactant ions with the carrier gas containing the target analytes until the detection signal for the adduct ions and/or analyte ions is above the signal background. In some embodiments, reactant ions move from the inlet to the detector by air flow, by an electric field, or by a combination of these approaches.

In some embodiments, resulting analyte ions and/or adduct ions can be introduced into the drift region 430 by a pulsing ion gate (not illustrated). Introduced analyte ions and/or adduct ions are then separated in drift region based upon mobility in the gas phase. Analyte ions and/or adduct ions can subsequently be detected at a Faraday plate (detector). Spectra generated subsequently include peaks in which mobility (observed as a function of drift time) can be linked to specific molecular species of interest. Intensity of the resulting peaks are related to concentration of the analyte ions and/or adduct ions of interest.

Figure 5A:
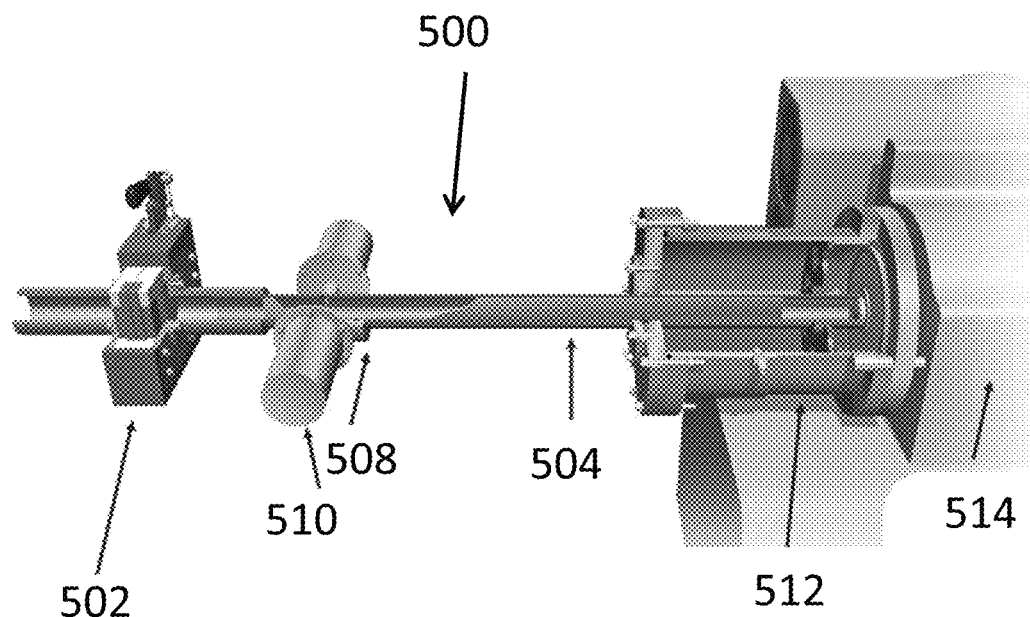
FIGS. 5A and 5B show another illustration of a representative system comprising a sample introduction region, two ionization sources, a split flow tube, an interface between the split flow tube and a detection apparatus.
Figure 5B:
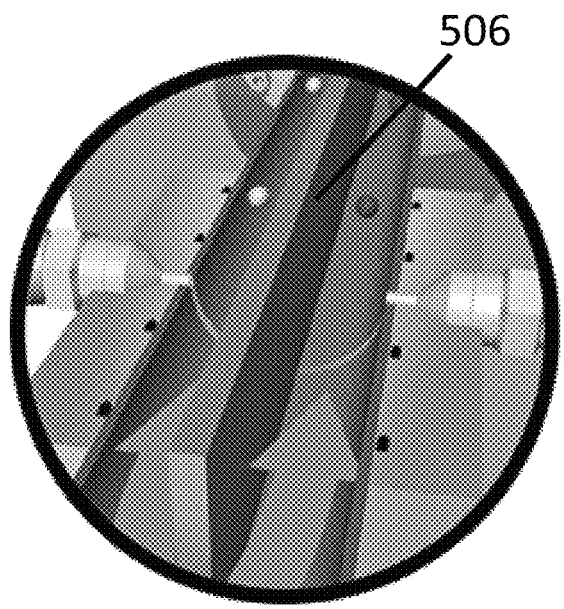

In some embodiments, multiple ionization sources can be used to produce different reactant ions that selectively or preferentially bind with target analytes of interest, such as those described above. A representative system comprising two ionization sources is illustrated in FIG. 5A. As illustrated in FIG. 5A, system 500 comprises a sample introduction region 502, which is coupled to split flow tube 504. A blown-up illustration of the inside of the split flow tube, which comprises barrier 506, is provided by FIG. 5B. System 500 further comprises two ionization sources, 508 and 510, that are coupled to split flow tube 504. An interface 512 can be used to couple split flow tube 504 to detection apparatus 514. Reactant ions that form selective stabilizing gas-phase complexes and/or selective chemical adduct ions can also be used. Reactant ions are also non-reactive with chemical species other than the target analyte of interest when introduced in a sample gas into the reaction region.

Target analytes that can be detected using the disclosed system and method embodiments are described herein. In some embodiments, target analytes can include chemical explosives, composite explosives, and chemicals used to identify presence of explosives [e.g., explosive taggants, such as 2,3-dimethyl-2,3-dinitrobutane (DMDNB)] and other threat agents. Exemplary composite explosive include, but are not limited to, SEMTEX, which is a general purpose plastic explosive containing cyclotrimethylenetrinitramine (RDX) (e.g., up to about 41% by weight) and pentaerythritol tetranitrate (PETN) (e.g., from about 40% to about 80% by weight), as well as plasticizers (e.g., n-octyl phthalate or tributyl citrate), binders (e.g., styrene-butadiene), stabilizers (e.g., N-phenyl-2-napthylamine), and dyes (e.g., diazo dye); SEMTEX analogs (e.g., SEMTEX-1A, SEMTEX-H, SEMTEX-2P); and C4, which is a plastic explosive containing RDX, a plasticizer (e.g., n-octyl phthalate or tributyl citrate), and a binder (e.g., styrene-butadiene). In some embodiments, the explosives or explosive compounds comprise a nitroamine chemical backbone, such as, but not limited to, RDX, 2,4,6-trinitrophenylmethylnitramine (TETRYL; also known as N-methyl-N,2,4,6-tetranitroaniline), cyclotetramethylene-tetranitramine (HMX), and the like. In some embodiments, the explosives or explosive compounds comprise a nitrate ester chemical backbone, such as, but not limited to, PETN, nitroglycerin (NG), ethylene glycol dinitrate (EGDN), and the like. In yet some additional embodiments, the explosives or explosive compounds comprise a nitroaromatic backbone, such as trinitrotoluene (TNT), picric acid, and 2,4,6-triamino-1,3,5-trinitrobenzene (TATB). The disclosed system and method embodiments also can be used to detect oxidizing salts used in explosive formulations, such as nitrate salts (e.g., ammonium nitrate, urea nitrate, and the like) and chlorate and/or perchlorate salts (e.g., potassium chlorate, potassium perchlorate, and the like).

In yet additional embodiments, the disclosed system and method embodiments can be used to determine the presence of OPCs, illicit drugs, and combinations thereof if present in a sample. An OPC is an organophosphate with various R-groups. In some embodiments, the organophosphorus compound is a phosphonate or an organophosphate with R groups typically containing between one and six carbons including, for example: dimethyl methyl phosphonate (DMMP), diisopropyl methyl phosphonate (DIMP), tributyl phosphate (TBP), triethyl phosphate (TEP), triphenylphosphate (TPhP), or combinations thereof. However, the present disclosure is not intended to be limited thereto. In some embodiments, the illicit drug may contain at least one functional group that is an amine. In some embodiments, the illicit drug is a secondary or tertiary amine. Representative illicit drugs include, but are not limited to heroin, cocaine, methamphetamine, opioids (e.g., fentanyl), opioid analogs, and other synthetic drugs (e.g., W-1 to W-32, such as W-18).

In some embodiments, one ionization source can be used to provide nitrate reactant ions ($NO_3^-$) (m/z=62) and nitrate-containing adduct ions, such as, but are not limited to, $NO_3^-.HNO_3$ (m/z=125); and $NO_3^-.H_2O)_x$ where x=1 to 4 (m/z=80, 98, 116, and 134, respectively). In some embodiments, nitrate ($NO_3^-$) (m/z=62) ions may be preferred reactant ions in one of the reaction regions given their selective binding to target analytes of interest. Nitrate ($NO_3^-$) has a high electron affinity that does not give up charge easily to most species in the gas phase. Thus, in some embodiments, nitrate ions can be used in one reaction region to form chemical adduct ions (selective complexes) with target analytes including, for example, gas-phase explosives and other threat agents described herein. $NO_3^-$ (m/z=62) may be created from any suitable discharge ionization source at selected pressures, and typically above 100 Torr. Electron affinity of the nitrate reactant ion typically means that the nitrate ion is not expected to give up its negative charge or otherwise participate in charge-exchange reactions. In some embodiments, however, chemical species (e.g., chlorates and perchlorates) may have a higher electron affinity and in such embodiments, the nitrate ion could interact with such species (e.g., potassium chlorate), thereby forming a chlorate anion.

Thus, selectivity is achieved since the only ionization mechanism available is the formation of chemical adduct ions between the nitrate reactant ion and the target analyte of interest. Further, selectivity is achieved since few analytes have a propensity to share this charge and to form stable chemical adduct ions. Thus, a reduction in chemical background is achieved while yielding chemical adduct ions with the analytes of interest.

In some embodiments, other reactant ions may be generated in the second reaction region at the same time that the nitrate ions are produced in the first reaction region. Such other reactant ions can include, but are not limited to chloride ($Cl^-$) ions, bromide ($Br^-$) ions, iodide ($I^-$) ions, nitrite ($NO_2^-$) ions, $O_2^-$, $CO_3^-$, or combinations of these ions. In some embodiments, these ions can be generated from the same carrier gas and/or the same type of ionization source used with the first reaction region. For example, a reverse flow method using an ionization source, such as that illustrated by FIG. 3, can be used to increase air flow in the ionization source such that the chemical make-up of the ions introduced into the split flow tube can be modified. By increasing the air flow rate (the maximum and minimum flow rates can depend on the internal volume of the ionization source or a container holding the ionization source), the ion chemistry present in the ionization source (and that is delivered to the split flow tube) can be changed from containing nitrate ions to containing other reactant ions, such as, but not limited to, chloride ($Cl^-$) ions, bromide ($Br^-$) ions, iodide ($I^-$) ions, nitrite ($NO_2$) ions, $O_2^-$, $Co_3^-$, or combinations of these ions. In one exemplary embodiment, reverse air flow is used to move away from nitrate ions and results in forming an ion having m/z=89. Without being limited to a single theory, it currently is believed that this ion may be formed from room air and may be an acid, such as lactic acid or oxalic acid. Even if this exemplary ion species does not participate in the ionization of TNT, which it may or may not, it provides confirmation that using the air flow allows for the ability to migrate away from nitrate ions towards $O_2^-$ ions. Controlling the air flow rates can be achieved using a reverse flow of air through the ionization source, wherein it is reversed as compared to the flow of ions passing from the ionization source to the split flow tube. By moving away from using nitrate ions or nitrate-containing ions in one of the reaction regions, different analytes can be detected that do not normally form adducts with nitrate ions or nitrate-containing ions, such as nitroaromatic species like TNT. In some embodiments, the flow rate can be increased by doubling, tripling, or quadrupling a standard flow rate used. In particular embodiments, a flow rate of 3 liters per minute (LPM) to 20 LPM, such as 3 LPM to 15 LPM, or 3 LPM to 11 LPM, can be used in the ionization source.

Figure 6:
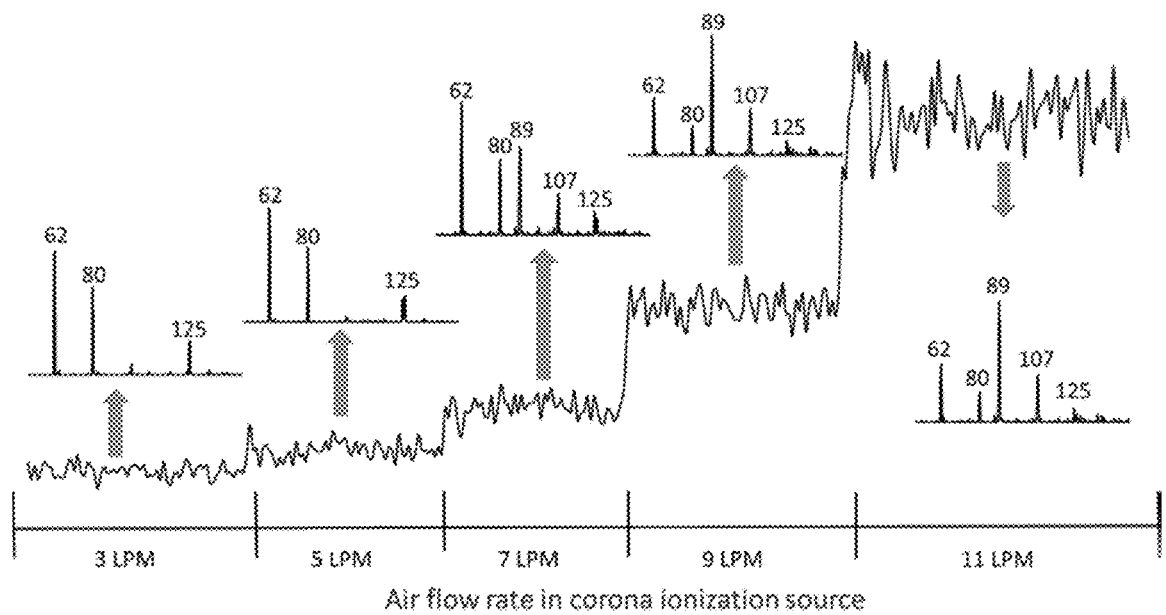
FIG. 6 is an illustration of how increasing air flow rate through a reverse corona discharge ionization source can change the chemical make-up of ions provided by the ionization source; the numbers listed for each peak represents the ion mass.

FIG. 6 provides a representative schematic illustrating how reverse air flow rates can be used to change the ion chemistry within an ionization source and/or reaction region. As illustrated in FIG. 6, as the air flow through the ionization source increases from 3 LPM to 11 LMP, the typical nitrate ion peak (m/z=62) or nitrate-containing ion peaks (m/z=80 and m/z=125) become less prevalent and ion peaks corresponding to other ions within in the ionization source (e.g., m/z=89 and m/z=107) become the dominant ion species for interaction with analytes in any sample vapor introduced into the split flow tube.

In some embodiments, the disclosed split flow tube can be used in a system wherein a sample (or combination of samples) is analyzed using nitrate (or nitrate-containing) reactant ions produced by a first ionization source and dopant and/or proton-bound dopant ions produced by a second ionization source. In this embodiment, the nitrate (or nitrate-containing) reactant ions are introduced into a first reaction region from the first ionization source and the dopant ions and/or proton-bound dopant ions are introduced into a second reaction region of the split flow tube. Any ions and/or vapors (produced from the sample or combination of samples) present in reaction regions are allowed to flow through their respective reaction region and thereby interact with each other to form detectable adduct ions and/or analyte ions. Any adducts ions and/or analyte ions formed between the ions and any analytes of interest in the different reaction regions may be detected with an associated detector. In a representative embodiment, this method can be used to detect an explosive (e.g., RDX, PETN, or the like) and an illicit drug or an OPC. In such embodiments, a detector apparatus that can detect negative and positive ions simultaneously, or substantially simultaneously can be used.

In yet another embodiment, reactant ions other than nitrate (or nitrate-containing) ions can be introduced into a first reaction region from a first ionization source. These reactant ions can be obtained using the reverse air flow method described herein to reduce the presence of nitrate (or nitrate-containing) ions. Dopant ions and/or proton-bound dopant ions can be introduced into a second reaction region of the split flow tube, typically from a dopant source. The reactant ions, dopant ions, and/or proton-bound dopant ions and vapors (produced from the sample or combination of samples) are allowed to flow through their respective reaction region and interact with each other to form detectable analyte species, such as adducts and/or ionized analyte species. Any analyte species formed between the reactant ions and any analytes of interest, and/or any analyte adducts formed between the dopant ions (or proton-bound dopant ions) and any analytes of interest, in the different reaction regions may be detected with an associated detector. In one representative embodiment, this method can be used to detect the presence of an explosive, such as TNT or TATB; and an illicit drug (or an OPC) using a single sampling event.

In yet another embodiment, a first dopant can be used in combination with sample vapors to form dopant adduct ions in one reaction region and a second dopant, which is different from the first dopant source, can be used in combination with sample vapors in another reaction region of the split flow tube to form other dopant adduct ions. As such, dopant adduct ions formed with the first dopant and dopant adduct ions formed with the second dopant can be detected. In some embodiments, both the first dopant and the second dopant can be different in terms of identity, but they can both be dopants that interact with illicit drugs. In yet additional embodiments, both the first dopant and the second dopant can be different in terms of identity, but they can both be dopants that interact with OPCs. In yet additional embodiments, the first dopant can be a dopant that interacts with an OPC and the second dopant can be a dopant that interacts with an illicit drug.

In yet another embodiment, a dopant and a first ionization source can be used in combination with sample vapors of drug sample to form dopant adduct ions in one reaction region of a split flow tube and reactant ions provided by a second ionization source can be used in combination with sample vapors from the drug sample to form analyte ions in a second reaction region of the split flow tube. In some embodiments, the dopant adduct ions and the analyte ions are detected using the positive ion mode of a detection device, such as a positive ion mass spectrometer. In some such embodiments, the drug sample may comprise a plurality of drugs. In some embodiments, certain drug species in the drug sample can be detected using the dopant ions and first ionization source, but may not be detectable using the reactant ions and second ionization source; or certain drug species in the drug sample can be detected using the reactant ions and second ionization source, but may not be detectable using the dopant ions and first ionization source. Thus, by using the split flow tube so that both types of ionization processes can be used, it is possible to simultaneously detect the presence of multiple drug species from the same sample without having to use two different sampling and ionization steps.

V. Overview of Several Embodiments

Disclosed herein are embodiments of a split flow tube, comprising: a distal end configured to be coupled to a detection apparatus; a proximal end; a barrier positioned within the split flow tube so as to separate an internal volume of the split flow tube into two or more reaction regions and extending along a length of the split flow tube; a first opening in the split flow tube that is configured to accept a first ionization source; a second opening in the split flow tube that is configured to accept a sample introduction inlet; and an exit opening formed at the distal end of the split flow tube.

In some embodiments, the barrier, the split flow tube, or both are comprised of a metal material.

In any or all of the above embodiments, the split flow tube is comprised of copper, stainless steel, brass, or combinations thereof.

In any or all of the above embodiments, the barrier does not extend the entire length of the split flow tube.

In any or all of the above embodiments, the split flow tube further comprises a third opening configured to accept a second ionization source.

In any or all of the above embodiments, the first opening and the third opening are located near the proximal end of the split flow tube and/or wherein the first opening and the second opening are diametrically opposed.

Also disclosed herein are embodiments of a system, comprising: a first ionization source; a second ionization source; a split flow tube (wherein the split flow tube comprises a distal end configured to be coupled to a detection apparatus; a proximal end; a barrier positioned within the split flow tube so as to separate an internal volume of the split flow tube into two or more reaction regions and extending along a length of the split flow tube; a first opening in the split flow tube that is physically coupled to the first ionization source; a second opening in the split flow tube that is configured to accept a sample introduction inlet; a third opening in the split flow tube that is physically coupled to the second ionization source; and an exit opening formed at the distal end of the split flow tube); a sample introduction region coupled to the sample introduction inlet of the split flow tube; and a detection apparatus coupled to the distal end of the split flow tube.

In some embodiments, the system further comprises one or more pumps connected to the split flow tube and/or the detection apparatus.

In any or all of the above system embodiments, the sample introduction region is configured to house one or more solid surfaces, solid samples, sample vapors, dopant sources, dopants, or any combination thereof and wherein sample vapors are produced using thermal desorption.

In any or all of the above system embodiments, the sample introduction region and the sample introduction inlet are positioned near the proximal end of the split flow tube and before the first opening and the third opening, relative to the proximal end; or wherein the sample introduction region and the sample introduction inlet are positioned near the proximal end of the split flow tube and after the first opening and the third opening, relative to the proximal end.

In any or all of the above system embodiments, the detection apparatus is a mass spectrometer, an ion mobility spectrometer, or a differential ion mobility spectrometer.

In any or all of the above system embodiments, the first ionization source and the second ionization source are the same or wherein the first ionization source and the second ionization source are different.

In any or all of the above system embodiments, the first ionization source is a corona discharge ionization source that comprises an air inlet and an air outlet configured to provide reverse air flow during ionization.

In any or all of the above system embodiments, the second ionization source is a dielectric barrier discharge ionization source.

Also disclosed herein are embodiments of a method, comprising: introducing, into the split flow tube of claim 1, (i) a sample vapor and (ii) one or more reactant ions, one or more dopants or ions thereof, or a combination of the one or more reactant ions and the one or more dopants or ions thereof; and determining, with a detection apparatus coupled to the split flow tube, the presence of an adduct ion and/or an analyte ion formed between an analyte present in the sample vapor and the one or more reactant ions, the one or more dopants or ions thereof, or the combination of the one or more reactant ions and the one or more dopants or ions thereof.

In some embodiments, the method further comprises introducing the one or more reactant ions, the one or more dopants or ions thereof, or the combination of the one or more reactant ions and the one or more dopants or ions thereof into the split flow tube using a first ionization source, a second ionization source, or both.

In any or all of the above method embodiments, both the first ionization source and the second ionization source are used and wherein the first ionization source is a corona discharge ionization source and the second ionization source is a dielectric barrier discharge ionization source.

In any or all of the above method embodiments, the method further comprises flowing air into an air inlet of the corona discharge ionization source at an air flow rate that facilitates removing certain reactant ions prior to entering the split flow tube and wherein the air flows in an opposite direction relative to ion flow from the corona discharge ionization course into the split flow tube.

In any or all of the above method embodiments, the sample vapor comprises vapors produced from an explosive, an explosive compound, an explosive taggant, an organophosphorus compound, an explosive composite, an illicit drug, or any combination thereof.

In any or all of the above method embodiments, (i) the adduct ion is a chemical adduct ion or a dopant adduct ion, wherein the chemical adduct ion comprises a reactant ion selected from a nitrate ion, a nitrate-containing ion, a chloride ion, a bromide ion, an iodide ion, a nitrite ion, $O_2^-$, $CO_3^-$, or any combination of these ions; and/or the dopant adduct ion comprises a secondary amine, a tertiary amine, or an ion thereof; and/or (ii) the analyte ion comprises an analyte species from which a proton has been abstracted.

In any or all of the above method embodiments, the adduct ion comprises a proton-bound dopant adduct formed between the analyte and the dopant, wherein the analyte is a secondary amine, a tertiary amine, or a combination thereof and the dopant is an organophosphorus compound.

In any or all of the above method embodiments, the adduct ion comprises a proton-bound dopant adduct formed between the analyte and the dopant, wherein the analyte is an organophosphorus compound or an illicit drug and the dopant is a secondary amine, a tertiary amine, or a combination thereof.

In any or all of the above method embodiments, the sample vapor is delivered to the split flow tube between the proximal end of the split flow tube and before the first opening and the third opening, relative to the proximal end; or wherein the sample vapor is delivered to the split flow tube between the proximal end of the split flow tube and after the first opening and the third opening, relative to the proximal end.

VI. Examples

In examples described below, a split flow tube comprising two reaction regions is used at room temperature. Heat is applied to desorb the sample into the vapor phase for introduction via a sample introduction inlet. In most examples, the flow rate down the split flow tube is a combined 7 L/minute (wherein the flow rate down each of the two reaction regions is ~3.5 L/minute). For examples using a reverse corona ionization source, the flow rates typically are in the range of 3 L/minute to 11 L/minute, with non-nitrate chemistry being observed above 9 L/minute.

Example 1

Figure 7:
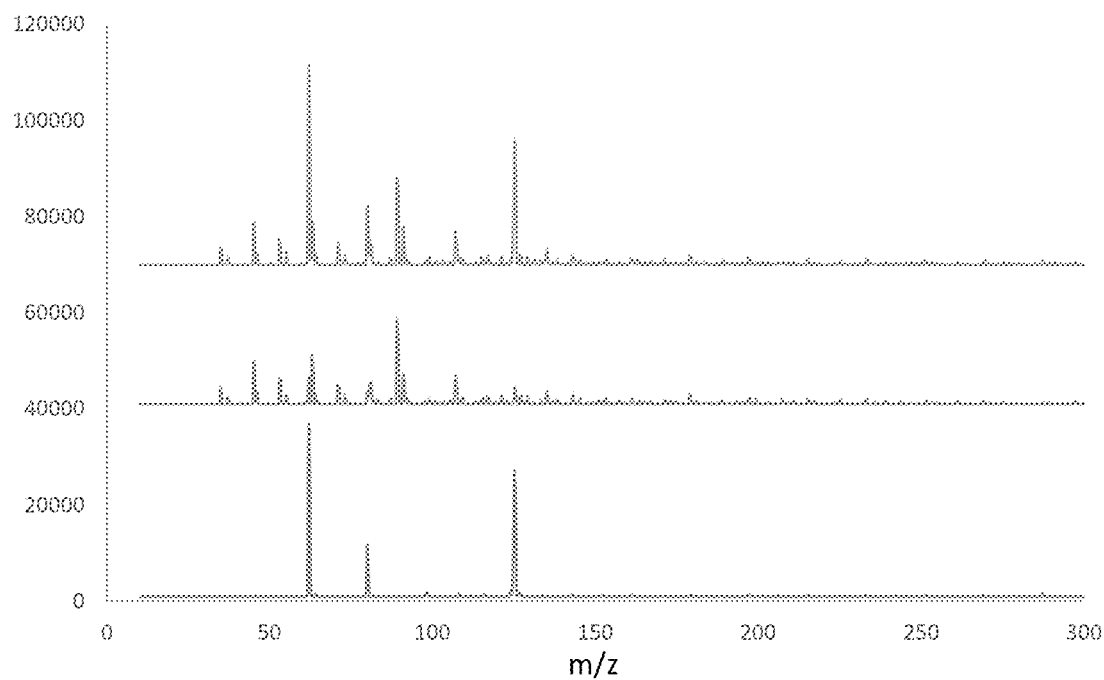
FIG. 7 is a combined mass spectrum showing results establishing that a split tube embodiment of the present disclosure can be used to analyze a sample using two different ionization sources with a single sampling event; the bottom spectrum shows the mass spectrum obtained from analyzing air using a dielectric barrier discharge (DBD) ionization source; the middle spectrum shows the mass spectrum obtained from analyzing air using a corona discharge ionization source; and the top spectrum shows the mass spectrum obtained from analyzing air with both the DBD and corona discharge sources using a single sampling event.

In this example, a system comprising a split flow tube coupled to a DBD ionization source and a corona discharge source was used to analyze background air. Results from this example are provided by FIG. 7. With reference to FIG. 7, three mass spectra are provided in a combined spectrum. The bottom spectrum shows detected ion peaks using the DBD ionization source. The middle spectrum shows detected ion peaks using the corona discharge source. The top spectrum shows ion peaks detected using both DBD and corona discharge sources at the same time with an embodiment of the split flow tube. As can be seen by FIG. 7, all peaks produced by using the two ionization sources independently can be observed by using these ionization sources at the same time.

Example 2

Figure 8A:
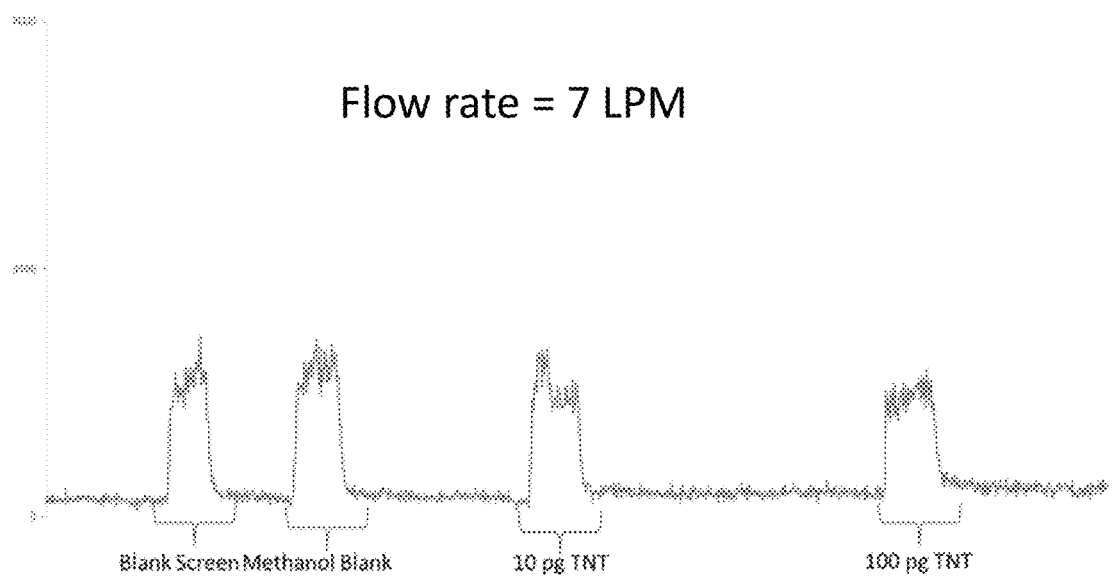
FIGS. 8A and 8B are selected ion mass spectra of a TNT proton abstracted ion ([M−H]⁻) at m/z=226, which show the effects of increasing reverse air flow rate in a reverse corona discharge ionization source; these figures show that the TNT analyte ion peak is not detected at 7 liters per minute (FIG. 8A), but upon increasing reverse air flow to 9 liters per minute, the TNT analyte ion peak (peak "A") is detected (FIG. 8B).
Figure 8B:
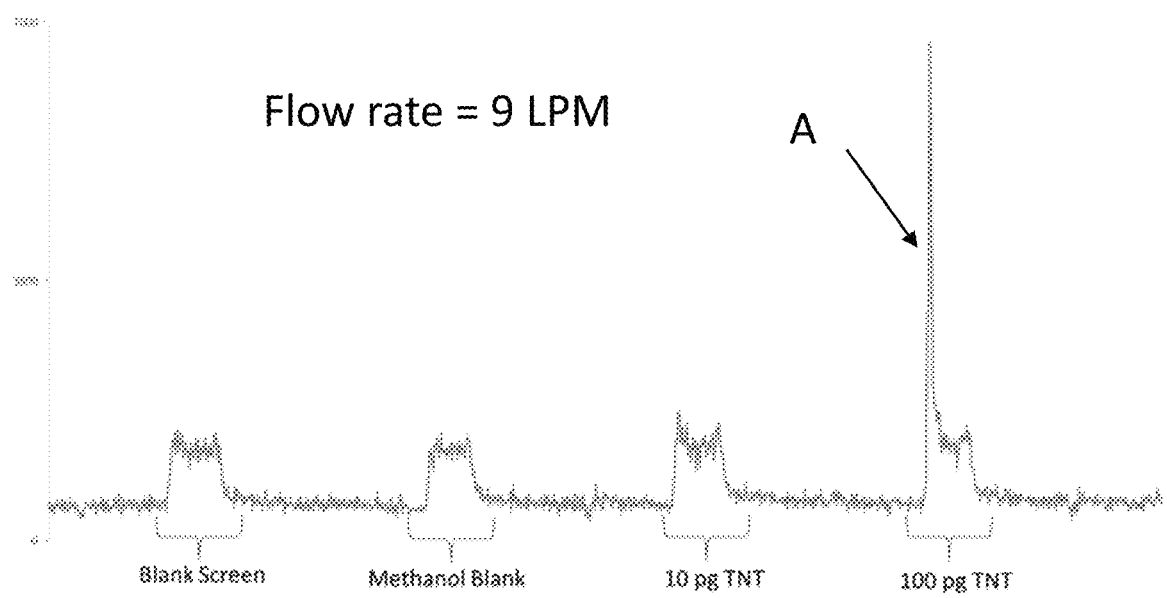

In this example, a reverse corona discharge ionization technique was used to detect the presence of 100 pg TNT in a sample and air flow rate through the ionization source was increased over time. As illustrated by FIGS. 8A and 8B, as air flow was increased from 7 LPM (FIG. 8A) to 9 LPM (FIG. 8B), TNT present in the sample becomes ionized by ions as the nitrate and/or nitrate-containing ions are forced away from the flow tube by the increased air flow. As such, other ions formed by the ionization step can interact with the TNT and remove a proton from its structure, resulting in an ionized (and detectable) TNT species (peak A in FIG. 8B)

Example 3

Figure 9A:
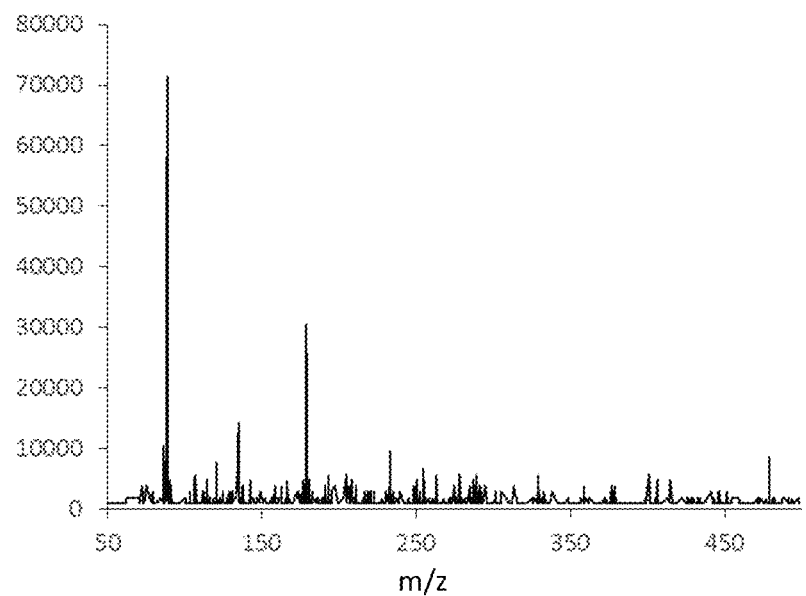
Figure 9B:
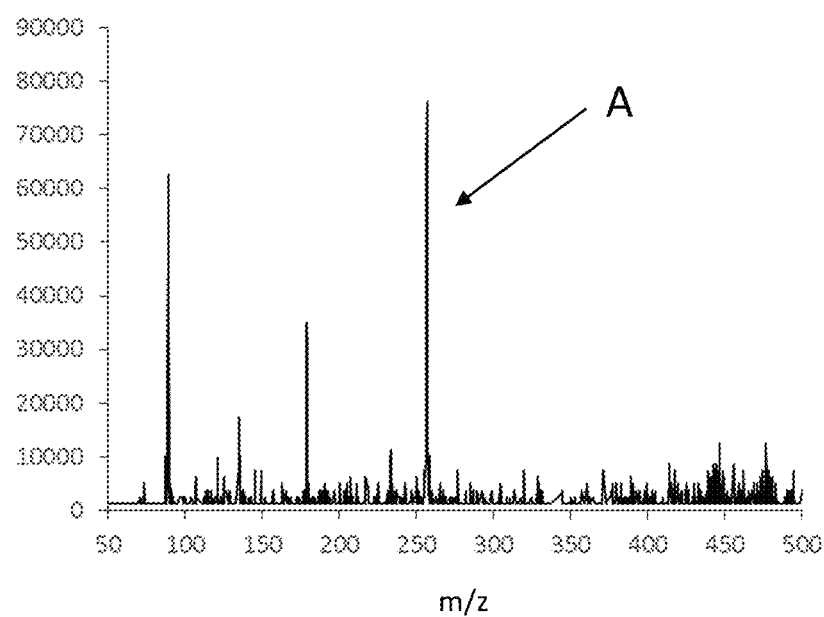

In this example, a reverse corona discharge ionization technique and a split flow tube was used to detect the presence of triaminotrinitrobenzene (also known as 2,4,6-triamino-1,3,5-trinitrobenzene or TATB), in a sample. TATB has a molecular weight of 258 and ionizes similar to TNT by proton abstraction providing an ion at m/z=257. FIGS. 9A and 9B provide mass spectra of both background (FIG. 9A) and 4 ng of TATB (FIG. 9B). Selected ion monitoring (not shown) demonstrated picogram detection levels of TATB.

Example 4

Figure 10:
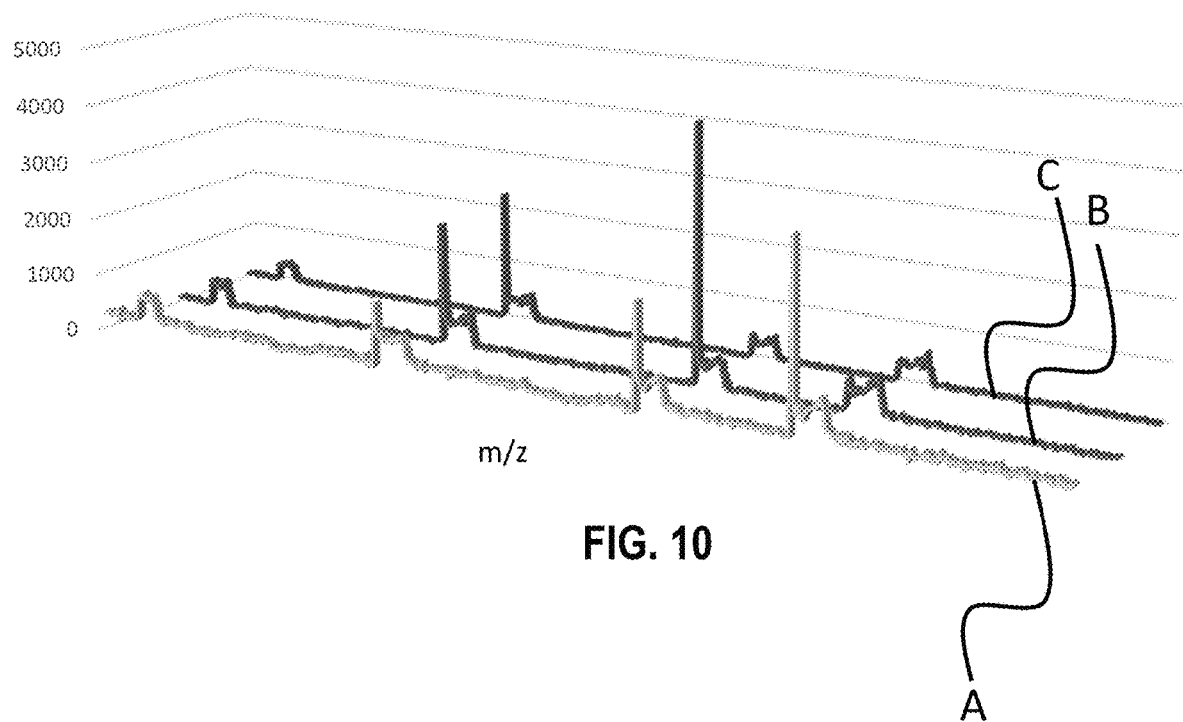
FIG. 10 is a combined spectrum providing three traces that represent single ion monitoring of the representative ions for TNT at m/z=226 (Trace A), RDX at m/z=284 (Trace B), and PETN at m/z=378 (Trace C).

In this example, a system comprising a split flow tube coupled to two ionization sources was used to simultaneously detect three explosive compounds present in a sample. The samples tested included (from left to right with reference to the peaks shown in FIG. 10) (i) a blank screen for a background sample, (ii) a mixture of TNT (100 pg), RDX, and PETN (50 pg total of RDX and PETN), (iii) a mixture of RDX (50 pg) and TNT (100 pg), and (iv) TNT only (100 pg). The three traces represent single ion monitoring of the representative ions for TNT at m/z=226 (FIG. 10, Trace A), RDX at m/z=284 (FIG. 10, Trace B), and PETN at m/z=378 (FIG. 10, Trace C). The small increase in baseline is due to heating the sample collection media the sharp peak at the leading edge represents detection of the analyte.

Example 5

In this example, a split flow tube and corresponding system is used to detect hexanitrohexaazaisowurtzitane (also known as CL-20) and TATB simultaneously using different ionization sources. The CL-20 is detected by coupling a first corona discharge ionization source configured to produce nitrate (or nitrate-containing) ions to the split flow tube and the TATB is detected by coupling a second corona discharge ionization source, which is configured to be operated as a reverse flow corona discharge ionization source so as to produce ions other than nitrate (or nitrate-containing ions), with the same split flow tube.

Example 6

In this example, a drug, such as heroin, and an explosive, such as hexamethylene triperoxide diamine (also known as HMTD) are detected simultaneously using a split flow tube and a corresponding system. The HMTD is detected using a triethylamine dopant in a first reaction regions of the split flow tube and the heroin is detected using a tributylphosphate dopant in a second reaction region of the split flow tube. The HMTD is detected at m/z=308 (which presumably corresponds to a cluster with protonated triethylamine with the loss of 2 hydrogen atoms ($[M+102-2H]^+$) and the heroin is detected at m/z=636 (which is the proton-bound adduct of heroin and TBP). Both species were detected as positive ions.

Example 7

Figure 11:
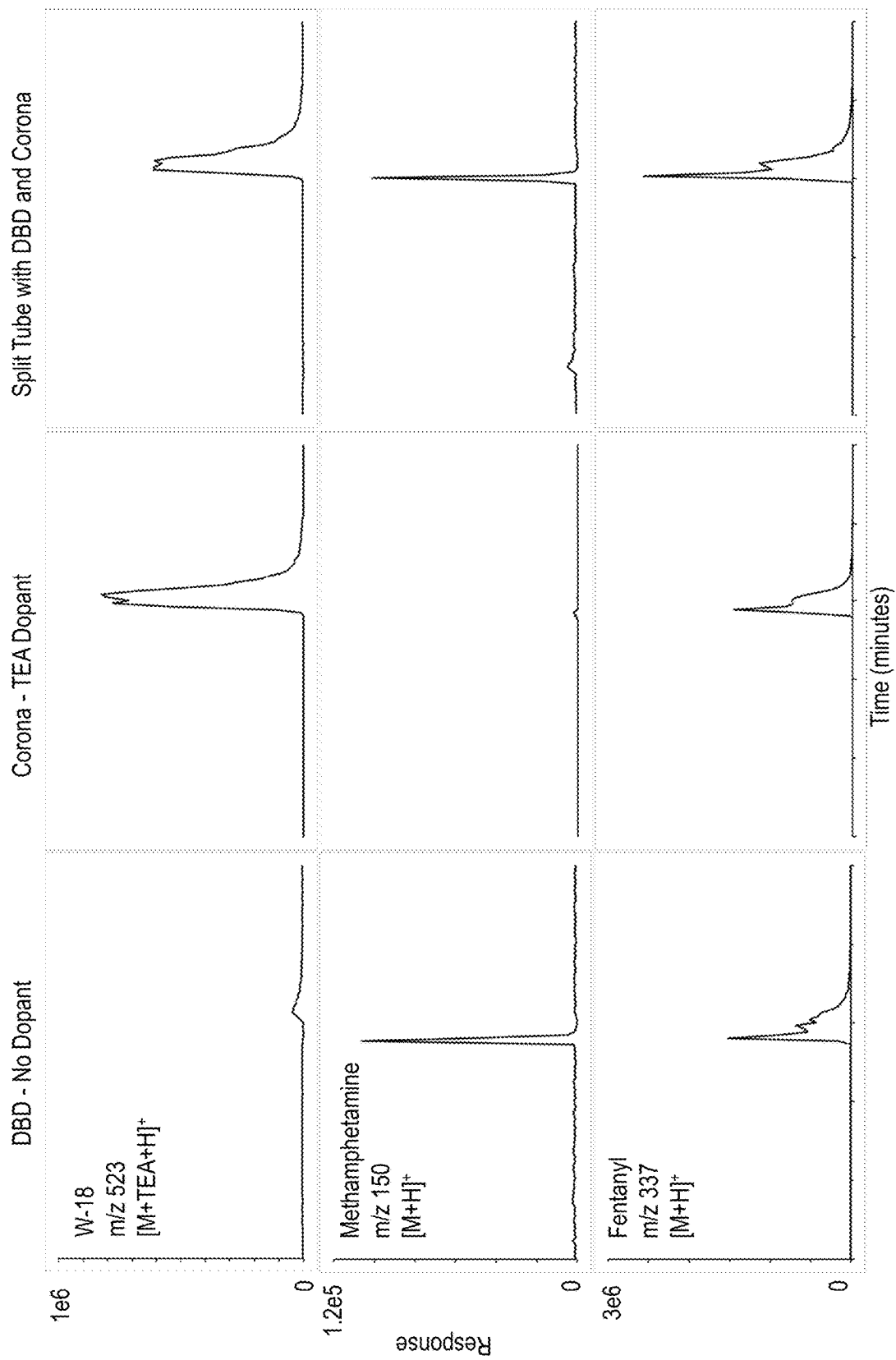
FIG. 11 is a combined spectrum of mass spectra obtained from analyzing a sample comprising three different illicit drugs species (W-18, methamphetamine, and fentanyl) using a DBD ionization technique (left column), a corona ionization technique (in combination with a triethylamine dopant) (middle column), and using both a DBD ionization technique and a corona ionization technique with a single sampling event and a split flow tube embodiment according to the present disclosure (right column).
Figure 12:
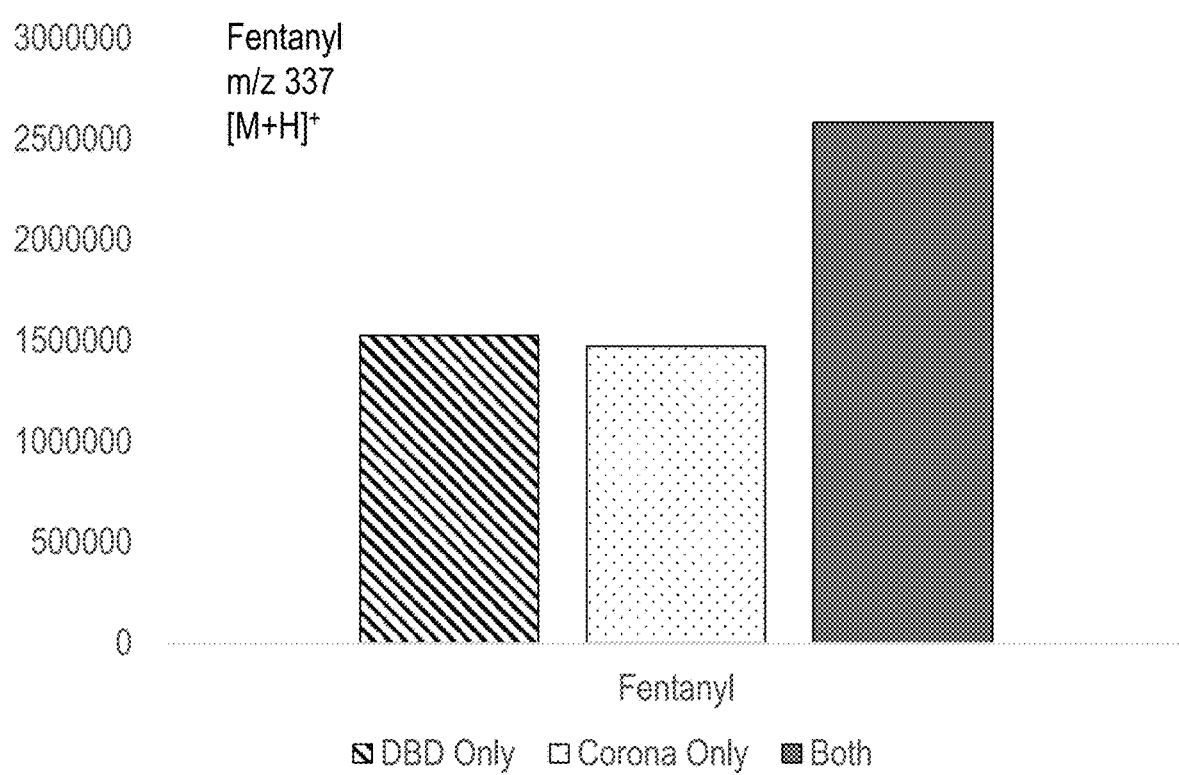
FIG. 12 is a bar graph summarizing the amount of fentanyl ions ([M+H]⁺) detected using DBD ionization only, corona ionization only (in combination with a triethylamine dopant), and both DBD and corona ionization with a split flow tube embodiment and a single sampling event.
Figure 13:
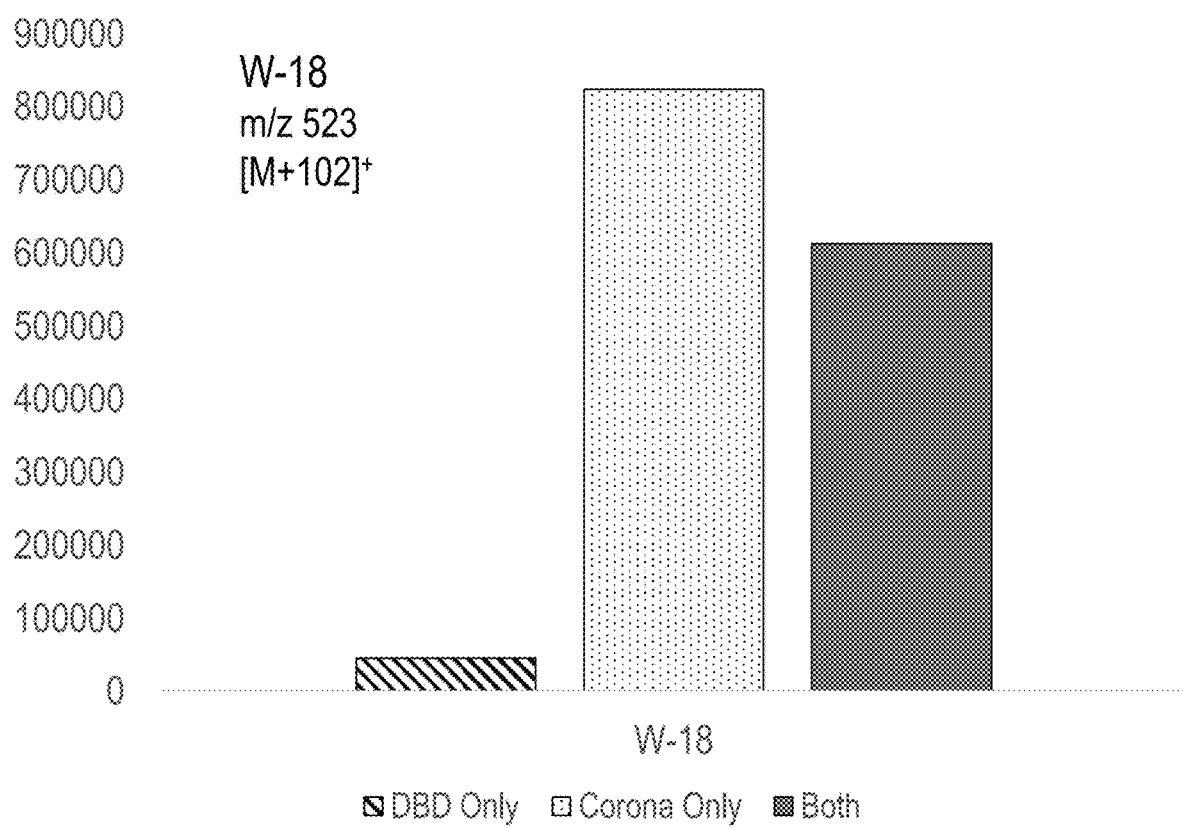
FIG. 13 is a bar graph summarizing the amount of W-18 ions ([M+101]⁺) detected using DBD ionization only, corona ionization only, and both DBD and corona ionization (in combination with a triethylamine dopant) with a split flow tube embodiment and a single sampling event.
Figure 14:
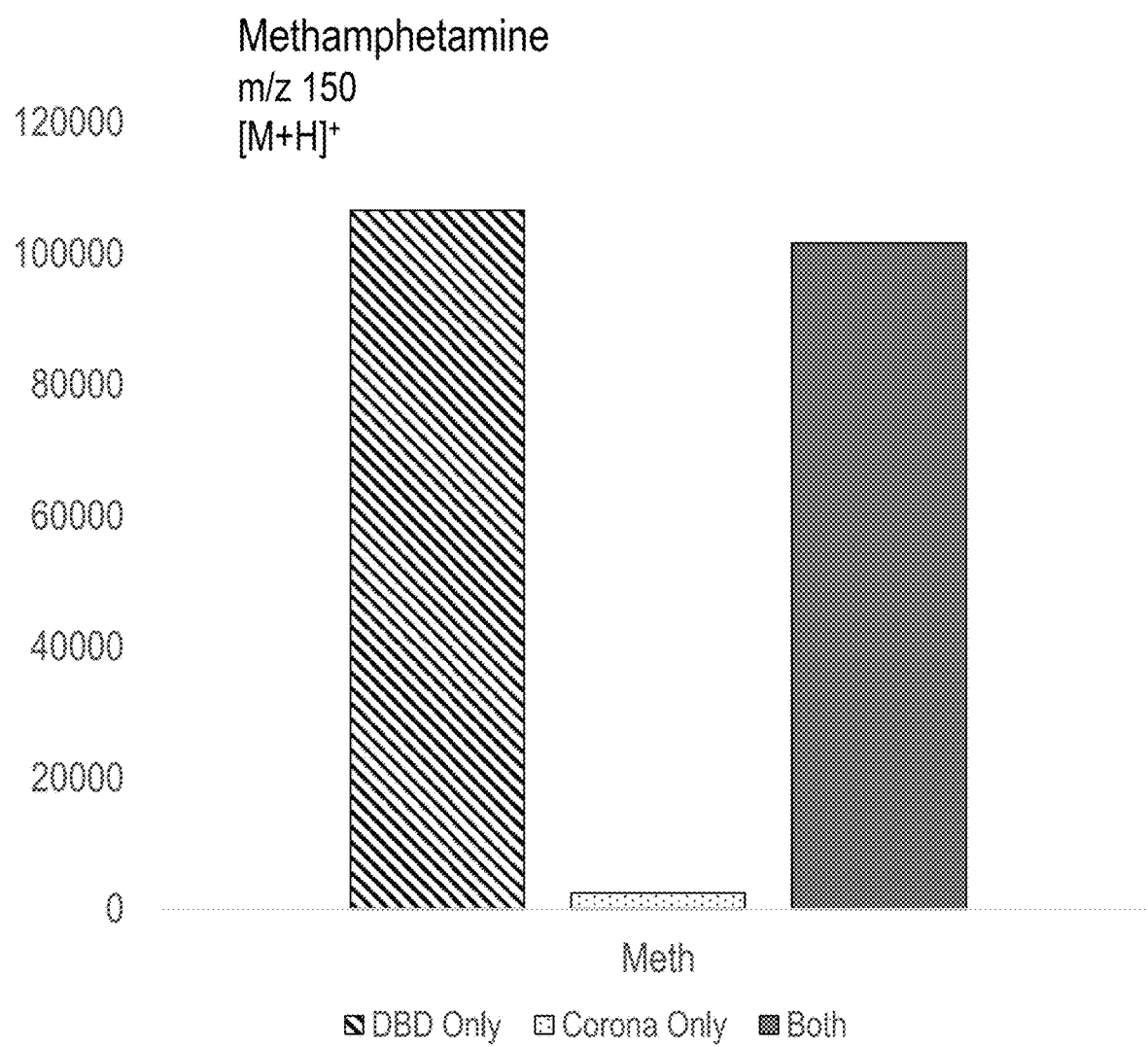
FIG. 14 is a bar graph summarizing the amount of methamphetamine ions ([M+H]⁺) detected using DBD ionization only, corona ionization only, and both DBD and corona ionization (in combination with a triethylamine dopant) with a split flow tube embodiment and a single sampling event.

In this example, a drug sample comprising 1 ng each of three different drugs, methamphetamine, fentanyl, and W-18, were detected simultaneously using a split flow tube and a corresponding system. Both the fentanyl and the methamphetamine were detected without a dopant in a first reaction region of the split flow tube, using a DBD ionization source. The drug sample was desorbed from a sample introduction region and both W-18 and fentanyl were detected using a triethylamine dopant in a second reaction region of the split flow tube, using a corona discharge ionization source. A mass spectrometer was used in positive ion detection mode to determine the presence of the W-18 (with a m/z=523, which represents the $[W-18+TEA+H]^+$ adduct), the methamphetamine (with a m/z=150, which represents the $[Meth+H]^+$ ion, and the fentanyl (with a m/z=337, which represents that $[Fentanyl+H]^+$ ion. Results are shown in FIGS. 11-14. FIG. 11 shows the combined mass spectra obtained from this example. The left column of spectra in FIG. 11 was obtained by analyzing a sample comprising all three drugs using only a DBD ionization source with no dopant. The middle column of spectra in FIG. 11 was obtained by analyzing the sample comprising all three drugs using only the corona ionization source with the triethylamine dopant. The right column of spectra in FIG. 11 was obtained by analyzing the sample comprising all three drugs using the split flow tube configured with both the DBD and corona ionization sources. As can be seen by the spectra of FIG. 11, using the split flow tube allows detection of all three analytes simultaneously. FIGS. 12-14 are bar graphs that provide a different representation of the results obtained from this example.

In view of the many possible embodiments to which the principles of the present disclosure may be applied, it should be recognized that the illustrated embodiments are only preferred examples and should not be taken as limiting. Rather, the scope of the present disclosure is defined by the following claims. We therefore claim as our invention all that comes within the scope and spirit of these claims.

We claim:
1. A split flow tube, comprising:
   a distal end configured to be coupled to a detection apparatus;
   a proximal end;
   a barrier positioned within the split flow tube so as to separate an internal volume of the split flow tube into two or more reaction regions and extending along a length of the split flow tube;

a first opening in the split flow tube that is configured to accept a first ionization source;

a second opening in the split flow tube that is configured to accept a sample introduction inlet; and an exit opening formed at the distal end of the split flow tube.

2. The split flow tube of claim 1, wherein the barrier, the split flow tube, or both are comprised of a metal material.

3. The split flow tube of claim 1, wherein the split flow tube is comprised of copper, stainless steel, brass, or combinations thereof.

4. The split flow tube of claim 1, wherein the barrier does not extend the entire length of the split flow tube.

5. The split flow tube of claim 1, further comprising a third opening configured to accept a second ionization source.

6. The split flow tube of claim 1, wherein the first opening and the third opening are located near the proximal end of the split flow tube and/or wherein the first opening and the second opening are diametrically opposed.

7. A system, comprising:
a first ionization source;
a second ionization source;
a split flow tube comprising
a distal end configured to be coupled to a detection apparatus;
a proximal end;
a barrier positioned within the split flow tube so as to separate an internal volume of the split flow tube into two or more reaction regions and extending along a length of the split flow tube;
a first opening in the split flow tube that is physically coupled to the first ionization source;
a second opening in the split flow tube that is configured to accept a sample introduction inlet;
a third opening in the split flow tube that is physically coupled to the second ionization source; and
an exit opening formed at the distal end of the split flow tube;
a sample introduction region coupled to the sample introduction inlet of the split flow tube; and
a detection apparatus coupled to the distal end of the split flow tube.

8. The system of claim 7, further comprising one or more pumps connected to the split flow tube and/or the detection apparatus.

9. The system of claim 7, wherein the sample introduction region is configured to house one or more solid surfaces, solid samples, sample vapors, dopant sources, dopants, or any combination thereof and wherein sample vapors are produced using thermal desorption.

10. The system of claim 7, wherein the sample introduction region and the sample introduction inlet are positioned near the proximal end of the split flow tube and before the first opening and the third opening, relative to the proximal end; or wherein the sample introduction region and the sample introduction inlet are positioned near the proximal end of the split flow tube and after the first opening and the third opening, relative to the proximal end.

11. The system of claim 7, wherein the detection apparatus is a mass spectrometer, an ion mobility spectrometer, or a differential ion mobility spectrometer.

12. The system of claim 7, wherein the first ionization source and the second ionization source are the same or wherein the first ionization source and the second ionization source are different.

13. The system of claim 7, wherein the first ionization source is a corona discharge ionization source that comprises an air inlet and an air outlet configured to provide reverse air flow during ionization.

14. The system of claim 7, wherein the second ionization source is a dielectric barrier discharge ionization source.

15. A method, comprising:
introducing, into the split flow tube of claim 1, (i) a sample vapor and (ii) one or more reactant ions, one or more dopants or ions thereof, or a combination of the one or more reactant ions and the one or more dopants or ions thereof; and
determining, with a detection apparatus coupled to the split flow tube, the presence of an adduct ion and/or an analyte ion formed between an analyte present in the sample vapor and the one or more reactant ions, the one or more dopants or ions thereof, or the combination of the one or more reactant ions and the one or more dopants or ions thereof.

16. The method of claim 15, further comprising introducing the one or more reactant ions, the one or more dopants or ions thereof, or the combination of the one or more reactant ions and the one or more dopants or ions thereof into the split flow tube using a first ionization source, a second ionization source, or both.

17. The method of claim 16, wherein both the first ionization source and the second ionization source are used and wherein the first ionization source is a corona discharge ionization source and the second ionization source is a dielectric barrier discharge ionization source.

18. The method of claim 17, further comprising flowing air into an air inlet of the corona discharge ionization source at an air flow rate that facilitates removing certain reactant ions prior to entering the split flow tube and wherein the air flows in an opposite direction relative to ion flow from the corona discharge ionization course into the split flow tube.

19. The method of claim 15, wherein the sample vapor comprises vapors produced from an explosive, an explosive compound, an explosive taggant, an organophosphorus compound, an explosive composite, an illicit drug, or any combination thereof.

20. The method of claim 15, wherein (i) the adduct ion is a chemical adduct ion or a dopant adduct ion, wherein the chemical adduct ion comprises a reactant ion selected from a nitrate ion, a nitrate-containing ion, a chloride ion, a bromide ion, an iodide ion, a nitrite ion, $O_2^-$, $CO_3^-$, or any combination of these ions; and/or the dopant adduct ion comprises a secondary amine, a tertiary amine, or an ion thereof; and/or (ii) the analyte ion comprises an analyte species from which a proton has been abstracted.

21. The method of claim 15, wherein the adduct ion comprises a proton-bound dopant adduct formed between the analyte and the dopant, wherein the analyte is a secondary amine, a tertiary amine, or a combination thereof and the dopant is an organophosphorus compound.

22. The method of claim 15, wherein the adduct ion comprises a proton-bound dopant adduct formed between the analyte and the dopant, wherein the analyte is an organophosphorus compound or an illicit drug and the dopant is a secondary amine, a tertiary amine, or a combination thereof.

23. The method of claim 15, wherein the sample vapor is delivered to the split flow tube between the proximal end of the split flow tube and before the first opening and the third opening, relative to the proximal end; or wherein the sample vapor is delivered to the split flow tube between the proximal end of the split flow tube and after the first opening and the third opening, relative to the proximal end.

* * * * *